United States Patent
Lee et al.

(10) Patent No.: US 11,782,509 B1
(45) Date of Patent: Oct. 10, 2023

(54) BRAINWAVE AUDIO AND VIDEO ENCODING AND PLAYING SYSTEM

(71) Applicants: Ching Lee, Taipei (TW); Ruey Yuan Lee, Taipei (TW)

(72) Inventors: Ching Lee, Taipei (TW); Ruey Yuan Lee, Taipei (TW)

( * ) Notice: Subject to any disclaimer, the term of this patent is extended or adjusted under 35 U.S.C. 154(b) by 0 days.

(21) Appl. No.: 17/748,046

(22) Filed: May 19, 2022

(51) Int. Cl.
*G06F 3/01* (2006.01)
*G10H 1/36* (2006.01)

(52) U.S. Cl.
CPC ............ *G06F 3/015* (2013.01); *G10H 1/361* (2013.01); *G10H 2220/376* (2013.01)

(58) Field of Classification Search
CPC ... G06F 3/015; G10H 1/361; G10H 2220/376
See application file for complete search history.

(56) References Cited

U.S. PATENT DOCUMENTS

| | | | |
|---|---|---|---|
| 2015/0338917 A1* | 11/2015 | Steiner | H04L 9/3271 345/156 |
| 2016/0103487 A1* | 4/2016 | Crawford | A61B 5/117 600/544 |

\* cited by examiner

*Primary Examiner* — Hang Lin

(57) ABSTRACT

A brainwave audio and video encoding and playing system is provided. Based on the research and understanding of the brainwaves, the relations of variations of the brainwaves corresponding to the melodies of the human voice senses and the relations of the human brainwaves to the colors is built so as to create rules for playing of the melodies by musical instrument and colors in a display so that variations of the brainwaves can be expressed by playing of music and display of colors and the messages of brainwaves could be transferred. As a result, the people have the same feeling to the testers.

14 Claims, 24 Drawing Sheets

|    | Att | Med | δ    | θ    | α⁻   | α⁺    | β⁻   | β⁺   | γ⁻   | γ⁺   |
|----|-----|-----|------|------|------|-------|------|------|------|------|
| D₁ | 7   | 5   | 21.2 | 28.1 | -7.5 | 31.4  | 0.6  | 13.6 | 27.3 | 9.7  |
| D₂ | -1  | -24 | 28.5 | 64   | 47.6 | -16.5 | 65.1 | 83.4 | 43.9 | 66.2 |
| D₃ | 6   | 0   | -34  | -83  | -27  | -12.1 | -58  | -87  | -67  | -63  |
| D₄ | 11  | -10 | 5.3  | 7    | 37.6 | 7.3   | -4.3 | 12.6 | 8.4  | -7   |
| D₅ | 10  | 11  | 20.8 | -3.9 | 59.7 | 87.8  | 35.7 | 34.3 | 60.4 | 16.9 |
| D₆ | -3  | 18  | 19.3 | 66   | 0    | -62   | 31   | -87  | 16.7 | 13.3 |
| D₇ | -4  | -2  | -30  | 13.7 | -89  | 62.2  | 51.3 | 7    | 0    | 56.1 |
| D₈ | 1   | 17  | -32  | -93  | -0.4 | -88   | -94  | -16  | 93.2 | -93  |

FIG. 4

|    | Att | Med | δ | θ | α⁻ | α⁺ | β⁻ | β⁺ | γ⁻ | γ⁺ |
|----|-----|-----|---|---|----|----|----|----|----|----|
| T₁ | 1   | 1   | 0 | 0 | 1  | 1  | 0  | 0  | 0  | 0  |
| T₂ | 1   | 0   | 1 | 1 | 1  | 0  | 1  | 1  | 1  | 1  |
| T₃ | 0   | 1   | 1 | 1 | 0  | 1  | 0  | 1  | 1  | 0  |
| T₄ | 0   | 1   | 0 | 1 | 0  | 0  | 1  | 0  | 0  | 1  |
| T₅ | 1   | 0   | 0 | 1 | 1  | 1  | 0  | 1  | 0  | 0  |
| T₆ | 0   | 1   | 1 | 0 | 0  | 1  | 1  | 1  | 0  | 0  |
| T₇ | 1   | 1   | 0 | 1 | 0  | 1  | 1  | 1  | 1  | 1  |

FIG. 5

|  | 1st note set | 2nd note set | 3rd note set | 4th note set |
|---|---|---|---|---|
| $T_1$ | $\delta(T_1,T_2,T_3)$<br>$=\delta(T_1)\times 2^2+\delta(T_2)\times 2$<br>$+\delta(T_3)$<br>$=0+2+1=3$<br><br>$\theta(T_1,T_2,T_3)$<br>$=\theta(T_1)\times 2^2+\theta(T_2)\times 2$<br>$+\theta(T_3)$<br>$=0+2+1=3$ | $(\alpha^-)(T_1,T_2,T_3)$<br>$=(\alpha^-)(T_1)\times 2^2+(\alpha^-)(T_2)\times 2$<br>$+(\alpha^-)(T_3)$<br>$=4+2+1=7$<br><br>$(\alpha^+)(T_1,T_2,T_3)$<br>$=(\alpha^+)(T_1)\times 2^2+(\alpha^+)(T_2)\times 2$<br>$+(\alpha^+)(T_3)$<br>$=4+0+1=5$ | $(\beta^-)(T_1,T_2,T_3)$<br>$=(\beta^-)(T_1)\times 2^2+(\beta^-)(T_2)\times 2$<br>$+(\beta^-)(T_3)$<br>$=0+2+1=3$<br><br>$(\beta^+)(T_1,T_2,T_3)$<br>$=(\beta^+)(T_1)\times 2^2+(\beta^+)(T_2)\times 2$<br>$+(\beta^+)(T_3)$<br>$=0+2+1=3$ | $(\gamma^-)(T_1,T_2,T_3)$<br>$=(\gamma^-)(T_1)\times 2^2+(\gamma^-)(T_2)\times 2$<br>$+(\gamma^-)(T_3)$<br>$=0+2+1=3$<br><br>$(\gamma^+)(T_1,T_2,T_3)$<br>$=(\gamma^+)(T_1)\times 2^2+(\gamma^+)(T_2)\times 2$<br>$+(\gamma^+)(T_3)$<br>$=0+2+0=2$ |
| $T_2$ | $\delta(T_2,T_3,T_4)$<br>$=\delta(T_2)\times 2^2+\delta(T_3)\times 2$<br>$+\delta(T_4)$<br>$=4+2+0=6$<br><br>$\theta(T_2,T_3,T_4)$<br>$=\theta(T_2)\times 2^2+\theta(T_3)\times 2$<br>$+\theta(T_4)$<br>$=4+2+1=7$ | $(\alpha^-)(T_2,T_3,T_4)$<br>$=(\alpha^-)(T_2)\times 2^2+(\alpha^-)(T_3)\times 2$<br>$+(\alpha^-)(T_4)$<br>$=4+2+0=6$<br><br>$(\alpha^+)(T_2,T_3,T_4)$<br>$=(\alpha^+)(T_2)\times 2^2+(\alpha^+)(T_3)\times 2$<br>$+(\alpha^+)(T_4)$<br>$=0+2+0=2$ | $(\beta^-)(T_2,T_3,T_4)$<br>$=(\beta^-)(T_2)\times 2^2+(\beta^-)(T_3)\times 2$<br>$+(\beta^-)(T_4)$<br>$=4+0+1=5$<br><br>$(\beta^+)(T_2,T_3,T_4)$<br>$=(\beta^+)(T_2)\times 2^2+(\beta^+)(T_3)\times 2$<br>$+(\beta^+)(T_4)$<br>$=4+2+0=6$ | $(\gamma^-)(T_2,T_3,T_4)$<br>$=(\gamma^-)(T_2)\times 2^2+(\gamma^-)(T_3)\times 2$<br>$+(\gamma^-)(T_4)$<br>$=4+2+0=6$<br><br>$(\gamma^+)(T_2,T_3,T_4)$<br>$=(\gamma^+)(T_2)\times 2^2+(\gamma^+)(T_3)\times 2$<br>$+(\gamma^+)(T_4)$<br>$=4+0+1=5$ |

FIG. 6A

| | 1st note set | 2nd note set | 3rd note set | 4th note set |
|---|---|---|---|---|
| $T_3$ | $\delta(T_3,T_4,T_5)$<br>$=\delta(T_3)\times 2^2+\delta(T_4)\times 2$<br>$+\delta(T_5)$<br>$=4+0+0=4$ | $(\alpha^-)(T_3,T_4,T_5)$<br>$=(\alpha^-)(T_3)\times 2^2+(\alpha^-)(T_4)\times 2$<br>$+(\alpha^-)(T_5)$<br>$=4+0+0=4$ | $(\beta^-)(T_3,T_4,T_5)$<br>$=(\beta^-)(T_3)\times 2^2+(\beta^-)(T_4)\times 2$<br>$+(\beta^-)(T_5)$<br>$=0+2+0=2$ | $(\gamma^-)(T_3,T_4,T_5)$<br>$=(\gamma^-)(T_3)\times 2^2+(\gamma^-)(T_4)\times 2$<br>$+(\gamma^-)(T_5)$<br>$=4+0+0=4$ |
| | $\theta(T_3,T_4,T_5)$<br>$=\theta(T_3)\times 2^2+\theta(T_4)\times 2$<br>$+\theta(T_5)$<br>$=4+2+1=7$ | $(\alpha^+)(T_3,T_4,T_5)$<br>$=(\alpha^+)(T_3)\times 2^2+(\alpha^+)(T_4)\times 2$<br>$+(\alpha^+)(T_5)$<br>$=4+0+1=5$ | $(\beta^+)(T_3,T_4,T_5)$<br>$=(\beta^+)(T_3)\times 2^2+(\beta^+)(T_4)\times 2$<br>$+(\beta^+)(T_5)$<br>$=4+0+1=5$ | $(\gamma^+)(T_3,T_4,T_5)$<br>$=(\gamma^+)(T_3)\times 2^2+(\gamma^+)(T_4)\times 2$<br>$+(\gamma^+)(T_5)$<br>$=0+2+0=2$ |
| $T_4$ | $\delta(T_4,T_5,T_6)$<br>$=\delta(T_4)\times 2^2+\delta(T_5)\times 2$<br>$+\delta(T_6)$<br>$=0+0+1=1$ | $(\alpha^-)(T_4,T_5,T_6)$<br>$=(\alpha^-)(T_4)\times 2^2+(\alpha^-)(T_5)\times 2$<br>$+(\alpha^-)(T_6)$<br>$=0+0+1=1$ | $(\beta^-)(T_4,T_5,T_6)$<br>$=(\beta^-)(T_4)\times 2^2+(\beta^-)(T_5)\times 2$<br>$+(\beta^-)(T_6)$<br>$=4+0+0=4$ | $(\gamma^-)(T_4,T_5,T_6)$<br>$=(\gamma^-)(T_4)\times 2^2+(\gamma^-)(T_5)\times 2$<br>$+(\gamma^-)(T_6)$<br>$=0+0+0=0$ |
| | $\theta(T_4,T_5,T_6)$<br>$=\theta(T_4)\times 2^2+\theta(T_5)\times 2$<br>$+\theta(T_6)$<br>$=4+2+0=6$ | $(\alpha^+)(T_4,T_5,T_6)$<br>$=(\alpha^+)(T_4)\times 2^2+(\alpha^+)(T_5)\times 2$<br>$+(\alpha^+)(T_6)$<br>$=0+2+1=3$ | $(\beta^+)(T_4,T_5,T_6)$<br>$=(\beta^+)(T_4)\times 2^2+(\beta^+)(T_5)\times 2$<br>$+(\beta^+)(T_6)$<br>$=0+2+1=3$ | $(\gamma^+)(T_4,T_5,T_6)$<br>$=(\gamma^+)(T_4)\times 2^2+(\gamma^+)(T_5)\times 2$<br>$+(\gamma^+)(T_6)$<br>$=4+0+0=4$ |
| $T_n$ | $\delta(T_n,T_{n+1},T_{n+2})$<br>$=\delta(T_n)\times 2^2+\delta(T_{n+1})\times 2$<br>$+\delta(T_{n+2})$ | $(\alpha^-)(T_n,T_{n+1},T_{n+2})$<br>$=(\alpha^-)(T_n)\times 2^2+(\alpha^-)(T_{n+1})\times 2$<br>$+(\alpha^-)(T_{n+2})$ | $(\beta^-)(T_n,T_{n+1},T_{n+2})$<br>$=(\beta^-)(T_n)\times 2^2+(\beta^-)(T_{n+1})\times 2$<br>$+(\beta^-)(T_{n+2})$ | $(\gamma^-)(T_n,T_{n+1},T_{n+2})$<br>$=(\gamma^-)(T_n)\times 2^2+(\gamma^-)(T_{n+1})\times 2$<br>$+(\gamma^-)(T_{n+2})$ |
| | $\theta(T_n,T_{n+1},T_{n+2})$<br>$=\theta(T_n)\times 2^2+\theta(T_{n+1})\times 2$<br>$+\theta(T_{n+2})$ | $(\alpha^+)(T_n,T_{n+1},T_{n+2})$<br>$=(\alpha^+)(T_n)\times 2^2+(\alpha^+)(T_{n+1})\times 2$<br>$+(\alpha^+)(T_{n+2})$ | $(\beta^+)(T_n,T_{n+1},T_{n+2})$<br>$=(\beta^+)(T_n)\times 2^2+(\beta^+)(T_{n+1})\times 2$<br>$+(\beta^+)(T_{n+2})$ | $(\gamma^+)(T_n,T_{n+1},T_{n+2})$<br>$=(\gamma^+)(T_n)\times 2^2+(\gamma^+)(T_{n+1})\times 2$<br>$+(\gamma^+)(T_{n+2})$ |

FIG. 6B

| | 1st note set | 2nd note set | 3rd note set |
|---|---|---|---|
| $T_1$ | $(Att)(T_1,T_2,T_3)$<br>$=(Att)(T_1)\times 2^2+(Att)(T_2)\times 2$<br>$+(Att)(T_3)$<br>$=4+2+0=6$<br><br>$(Med)(T_1,T_2,T_3)$<br>$=(Med)(T_1)\times 2^2+(Med)(T_2)\times 2$<br>$+(Med)(T_3)$<br>$=4+0+1=5$ | $T_1(\delta,\theta,\alpha^-)$<br>$=(\delta)(T_1)\times 2^2+(\theta)(T_1)\times 2+(\alpha^-)(T_1)$<br>$=0+0+1=1$<br><br>$T_1(\theta,\alpha^-,\alpha^+)$<br>$=(\theta)(T_1)\times 2^2+(\alpha^-)(T_1)\times 2+(\alpha^+)(T_1)$<br>$=0+2+1=3$<br><br>$T_1(\alpha^-,\alpha^+,\beta^-)$<br>$=(\alpha^-)(T_1)\times 2^2+(\alpha^+)(T_1)\times 2+(\beta^-)(T_1)$<br>$=4+2+0=6$<br><br>$T_1(\alpha^+,\beta^-,\beta^+)$<br>$=(\alpha^+)(T_1)\times 2^2+(\beta^-)(T_1)\times 2+(\beta^+)(T_1)$<br>$=4+0+0=4$<br><br>$T_1(\beta^-,\beta^+,\gamma^-)$<br>$=(\beta^-)(T_1)\times 2^2+(\beta^+)(T_1)\times 2+(\gamma^-)(T_1)$<br>$=0+0+0=0$<br><br>$T_1(\beta^+,\gamma^-,\gamma^+)$<br>$=(\beta^+)(T_1)\times 2^2+(\gamma^-)(T_1)\times 2+(\gamma^+)(T_1)$<br>$=0+0+0=0$ | $(\delta)(T_1,T_2,T_3)$<br>$=(\delta)(T_1)\times 2^2+(\delta)(T_2)\times 2+(\delta)(T_3)$<br>$=0+2+1=3$<br><br>$(\theta)(T_1,T_2,T_3)$<br>$=(\theta)(T_1)\times 2^2+(\theta)(T_2)\times 2+(\theta)(T_3)$<br>$=0+2+1=3$<br><br>$(\alpha^-)(T_1,T_2,T_3)$<br>$=(\alpha^-)(T_1)\times 2^2+(\alpha^-)(T_2)\times 2+(\alpha^-)(T_3)$<br>$=4+2+1=7$<br><br>$(\alpha^+)(T_1,T_2,T_3)$<br>$=(\alpha^+)(T_1)\times 2^2+(\alpha^+)(T_2)\times 2+(\alpha^+)(T_3)$<br>$=4+0+1=5$<br><br>$(\beta^-)(T_1,T_2,T_3)$<br>$=(\beta^-)(T_1)\times 2^2+(\beta^-)(T_2)\times 2+(\beta^-)(T_3)$<br>$=0+2+0=2$<br><br>$(\beta^+)(T_1,T_2,T_3)$<br>$=(\beta^+)(T_1)\times 2^2+(\beta^+)(T_2)\times 2+(\beta^+)(T_3)$<br>$=0+2+1=3$ |

FIG. 7A

| | 1st note set | 2nd note set | 3rd note set |
|---|---|---|---|
| $T_1$ | | $T_1(\gamma^-, \gamma^+, \delta)$<br>$=(\gamma^-)(T_1) \times 2^2 + (\gamma^+)(T_1) \times 2 + (\delta)(T_1)$<br>$= 0+0+0 = 0$<br><br>$T_1(\gamma^+, \delta^+, \theta)$<br>$=(\gamma^+)(T_1) \times 2^2 + (\delta^+)(T_1) \times 2 + (\theta)(T_1)$<br>$= 0+0+0 = 0$ | $(\gamma^-)(T_1, T_2, T_3)$<br>$=(\gamma^-)(T_1) \times 2^2 + (\gamma^-)(T_2) \times 2 + (\gamma^-)(T_3)$<br>$= 0+2+1 = 3$<br><br>$(\gamma^+)(T_1, T_2, T_3)$<br>$=(\gamma^+)(T_1) \times 2^2 + (\gamma^+)(T_2) \times 2 + (\gamma^+)(T_3)$<br>$= 0+2+0 = 2$ |
| $T_2$ | $(Att)(T_2, T_3, T_4)$<br>$=(Att)(T_2) \times 2^2 + (Att)(T_3) \times 2$<br>$+ (Att)(T_4)$<br>$= 4+0+0 = 4$<br><br>$(Med)(T_2, T_3, T_4)$<br>$=(Med)(T_2) \times 2^2 + (Med)(T_3) \times 2$<br>$+ (Med)(T_4)$<br>$= 0+2+1 = 3$ | $T_2(\delta, \theta, \alpha^-)$<br>$=(\delta)(T_2) \times 2^2 + (\theta)(T_2) \times 2 + (\alpha^-)(T_2)$<br>$= 4+2+1 = 7$<br><br>$T_2(\theta, \alpha^-, \alpha^+)$<br>$=(\theta)(T_2) \times 2^2 + (\alpha^-)(T_2) \times 2 + (\alpha^+)(T_2)$<br>$= 4+2+0 = 6$<br><br>$T_2(\alpha^-, \alpha^+, \beta^-)$<br>$=(\alpha^-)(T_2) \times 2^2 + (\alpha^+)(T_2) \times 2 + (\beta^-)(T_2)$<br>$= 4+0+1 = 5$<br><br>$T_2(\alpha^+, \beta^-, \beta^+)$<br>$=(\alpha^+)(T_2) \times 2^2 + (\beta^-)(T_2) \times 2 + (\beta^+)(T_2)$<br>$= 0+2+1 = 3$ | $(\delta)(T_2, T_3, T_4)$<br>$=(\delta)(T_2) \times 2^2 + (\delta)(T_3) \times 2 + (\delta)(T_4)$<br>$= 4+2+0 = 6$<br><br>$(\theta)(T_2, T_3, T_4)$<br>$=(\theta)(T_2) \times 2^2 + (\theta)(T_3) \times 2 + (\theta)(T_4)$<br>$= 4+2+1 = 7$<br><br>$(\alpha^-)(T_2, T_3, T_4)$<br>$=(\alpha^-)(T_2) \times 2^2 + (\alpha^-)(T_3) \times 2 + (\alpha^-)(T_4)$<br>$= 4+2+0 = 6$<br><br>$(\alpha^+)(T_2, T_3, T_4)$<br>$=(\alpha^+)(T_2) \times 2^2 + (\alpha^+)(T_3) \times 2 + (\alpha^+)(T_4)$<br>$= 0+2+0 = 2$ |

FIG. 7B

| | 1st note set | 2nd note set | 3rd note set |
|---|---|---|---|
| $T_2$ | | $T_2(\beta^-,\beta^+,\gamma^-)$<br>$=(\beta^-)(T_2)\times 2^2+(\beta^+)(T_2)\times 2+(\gamma^-)(T_2)$<br>$=4+2+1=7$<br><br>$T_2(\beta^+,\gamma^-,\gamma^+)$<br>$=(\beta^+)(T_2)\times 2^2+(\gamma^-)(T_2)\times 2+(\gamma^+)(T_2)$<br>$=4+2+1=7$<br><br>$T_2(\gamma^-,\gamma^+,\delta)$<br>$=(\gamma^-)(T_2)\times 2^2+(\gamma^+)(T_2)\times 2+(\delta)(T_2)$<br>$=4+2+1=7$<br><br>$T_2(\gamma^+,\delta,\theta)$<br>$=(\gamma^+)(T_2)\times 2^2+(\delta)(T_2)\times 2+(\theta)(T_2)$<br>$=4+2+1=7$ | $(\beta^-)(T_2,T_3,T_4)$<br>$=(\beta^-)(T_2)\times 2^2+(\beta^-)(T_3)\times 2+(\beta^-)(T_4)$<br>$=4+0+1=5$<br><br>$(\beta^+)(T_2,T_3,T_4)$<br>$=(\beta^+)(T_2)\times 2^2+(\beta^+)(T_3)\times 2+(\beta^+)(T_4)$<br>$=4+2+0=6$<br><br>$(\gamma^-)(T_2,T_3,T_4)$<br>$=(\gamma^-)(T_2)\times 2^2+(\gamma^-)(T_3)\times 2+(\gamma^-)(T_4)$<br>$=4+2+0=6$<br><br>$(\gamma^+)(T_2,T_3,T_4)$<br>$=(\gamma^+)(T_2)\times 2^2+(\gamma^+)(T_3)\times 2+(\gamma^+)(T_4)$<br>$=4+0+1=5$ |
| $T_3$ | $(Att)(T_3,T_4,T_5)$<br>$=(Att)(T_3)\times 2^2+(Att)(T_4)\times 2$<br>$+(Att)(T_5)$<br>$=0+0+1=1$<br><br>$(Med)(T_3,T_4,T_5)$<br>$=(Med)(T_3)\times 2^2+(Med)(T_4)\times 2$<br>$+(Med)(T_5)$<br>$=4+2+0=6$ | $T_3(\delta,\theta,\alpha^-)$<br>$=(\delta)(T_3)\times 2^2+(\theta)(T_3)\times 2+(\alpha^-)(T_3)$<br>$=4+2+1=7$<br><br>$T_3(\theta,\alpha^-,\alpha^+)$<br>$=(\theta)(T_3)\times 2^2+(\alpha^-)(T_3)\times 2+(\alpha^+)(T_3)$<br>$=4+2+1=7$ | $(\delta)(T_3,T_4,T_5)$<br>$=(\delta)(T_3)\times 2^2+(\delta)(T_4)\times 2+(\delta)(T_5)$<br>$=4+0+0=4$<br><br>$(\theta)(T_3,T_4,T_5)$<br>$=(\theta)(T_3)\times 2^2+(\theta)(T_4)\times 2+(\theta)(T_5)$<br>$=4+2+1=7$ |

FIG. 7C

| | 1st note set | 2nd note set | 3rd note set |
|---|---|---|---|
| $T_3$ | | $T_3(\alpha^-,\alpha^+,\beta^-)$<br>$=(\alpha^-)(T_3)\times 2^2+(\alpha^+)(T_3)\times 2+(\beta^-)(T_3)$<br>$=4+2+0=6$ | $(\alpha^-)(T_3,T_4,T_5)$<br>$=(\alpha^-)(T_3)\times 2^2+(\alpha^-)(T_4)\times 2+(\alpha^-)(T_5)$<br>$=4+0+0=4$ |
| | | $T_3(\alpha^+,\beta^-,\beta^+)$<br>$=(\alpha^+)(T_3)\times 2^2+(\beta^-)(T_3)\times 2+(\beta^+)(T_3)$<br>$=4+0+1=5$ | $(\alpha^+)(T_3,T_4,T_5)$<br>$=(\alpha^+)(T_3)\times 2^2+(\alpha^+)(T_4)\times 2+(\alpha^+)(T_5)$<br>$=4+0+1=5$ |
| | | $T_3(\beta^-,\beta^+,\gamma^-)$<br>$=(\beta^-)(T_3)\times 2^2+(\beta^+)(T_3)\times 2+(\gamma^-)(T_3)$<br>$=0+2+1=3$ | $(\beta^-)(T_3,T_4,T_5)$<br>$=(\beta^-)(T_3)\times 2^2+(\beta^-)(T_4)\times 2+(\beta^-)(T_5)$<br>$=0+2+0=2$ |
| | | $T_3(\beta^+,\gamma^-,\gamma^+)$<br>$=(\beta^+)(T_3)\times 2^2+(\gamma^-)(T_3)\times 2+(\gamma^+)(T_3)$<br>$=4+2+0=6$ | $(\beta^+)(T_3,T_4,T_5)$<br>$=(\beta^+)(T_3)\times 2^2+(\beta^+)(T_4)\times 2+(\beta^+)(T_5)$<br>$=4+0+1=5$ |
| | | $T_3(\gamma^-,\gamma^+,\delta)$<br>$=(\gamma^-)(T_3)\times 2^2+(\gamma^+)(T_3)\times 2+(\delta)(T_3)$<br>$=4+0+1=5$ | $(\gamma^-)(T_3,T_4,T_5)$<br>$=(\gamma^-)(T_3)\times 2^2+(\gamma^-)(T_4)\times 2+(\gamma^-)(T_5)$<br>$=4+0+0=4$ |
| | | $T_3(\gamma^+,\delta,\theta)$<br>$=(\gamma^+)(T_3)\times 2^2+(\delta)(T_3)\times 2+(\theta)(T_3)$<br>$=0+2+1=3$ | $(\gamma^+)(T_3,T_4,T_5)$<br>$=(\gamma^+)(T_3)\times 2^2+(\gamma^+)(T_4)\times 2+(\gamma^+)(T_5)$<br>$=0+2+0=2$ |

FIG. 7D

| | 1st note set | 2nd note set | 3rd note set |
|---|---|---|---|
| $T_n$ | $(Att)(T_n, T_{n+1}, T_{n+2})$<br>$=(Att)(T_n)\times 2^2+(Att)(T_{n+1})\times 2$<br>$+(Att)(T_{n+2})$<br><br>$(Med)(T_n, T_{n+1}, T_{n+2})$<br>$=(Med)(T_n)\times 2^2+(Med)(T_{n+1})\times 2$<br>$+(Med)(T_{n+2})$ | $T_n(\delta, \theta, \alpha^-)$<br>$(\delta)(T_n)\times 2^2+(\theta)(T_n)\times 2+(\alpha^-)(T_n)$<br><br>$T_n(\theta, \alpha^-, \alpha^+)$<br>$=(\theta)(T_n)\times 2^2+(\alpha^-)(T_n)\times 2+(\alpha^+)(T_n)$<br><br>$T_n(\alpha^-, \alpha^+, \beta^-)$<br>$=(\alpha^-)(T_n)\times 2^2+(\alpha^+)(T_n)\times 2+(\beta^-)(T_n)$<br><br>$T_n(\alpha^+, \beta^-, \beta^+)$<br>$=(\alpha^+)(T_n)\times 2^2+(\beta^-)(T_n)\times 2+(\beta^+)(T_n)$<br><br>$T_n(\beta^-, \beta^+, \gamma^-)$<br>$=(\beta^-)(T_n)\times 2^2+(\beta^+)(T_n)\times 2+(\gamma^-)(T_n)$<br><br>$T_n(\beta^+, \gamma^-, \gamma^+)$<br>$=(\beta^+)(T_n)\times 2^2+(\gamma^-)(T_n)\times 2+(\gamma^+)(T_n)$<br><br>$T_n(\gamma^-, \gamma^+, \delta)$<br>$=(\gamma^-)(T_n)\times 2^2+(\gamma^+)(T_n)\times 2+(\delta)(T_n)$<br><br>$T_n(\gamma^+, \delta^+, \theta)$<br>$=(\gamma^+)(T_n)\times 2^2+(\delta^+)(T_n)\times 2+(\theta)(T_n)$ | $(\delta)(T_n, T_{n+1}, T_{n+2})$<br>$=(\delta)(T_n)\times 2^2+(\delta)(T_{n+1})\times 2+(\delta)(T_{n+2})$<br><br>$(\theta)(T_n, T_{n+1}, T_{n+2})$<br>$=(\theta)(T_n)\times 2^2+(\theta)(T_{n+1})\times 2+(\theta)(T_{n+2})$<br><br>$(\alpha^-)(T_n, T_{n+1}, T_{n+2})$<br>$=(\alpha^-)(T_n)\times 2^2+(\alpha^-)(T_{n+1})\times 2+(\alpha^-)(T_{n+2})$<br><br>$(\alpha^+)(T_n, T_{n+1}, T_{n+2})$<br>$=(\alpha^+)(T_n)\times 2^2+(\alpha^+)(T_{n+1})\times 2+(\alpha^+)(T_{n+2})$<br><br>$(\beta^-)(T_n, T_{n+1}, T_{n+2})$<br>$=(\beta^-)(T_n)\times 2^2+(\beta^-)(T_{n+1})\times 2+(\beta^-)(T_{n+2})$<br><br>$(\beta^+)(T_n, T_{n+1}, T_{n+2})$<br>$=(\beta^+)(T_n)\times 2^2+(\beta^+)(T_{n+1})\times 2+(\beta^+)(T_{n+2})$<br><br>$(\gamma^-)(T_n, T_{n+1}, T_{n+2})$<br>$=(\gamma^-)(T_n)\times 2^2+(\gamma^-)(T_{n+1})\times 2+(\gamma^-)(T_{n+2})$<br><br>$(\gamma^+)(T_n, T_{n+1}, T_{n+2})$<br>$=(\gamma^+)(T_n)\times 2^2+(\gamma^+)(T_{n+1})\times 2+(\gamma^+)(T_{n+2})$ |

FIG. 7E

| | 1st note set | 2nd note set | 3rd note set | 4th note set |
|---|---|---|---|---|
| $T_1$ | $(Att)(T_1,T_2,T_3)$<br>$=(Att)(T_1)\times 2^2$<br>$+(Att)(T_2)\times 2$<br>$+(Att)(T_3)$<br>$=4+2+0=6$<br><br>$(Med)(T_1,T_2,T_3)$<br>$=(Med)(T_1)\times 2^2$<br>$+(Med)(T_2)\times 2$<br>$+(Med)(T_3)$<br>$=4+0+1=5$ | $T_1(\delta,\theta,\alpha^-)$<br>$=(\delta)(T_1)\times 2^2+(\theta)(T_1)\times 2+(\alpha^-)(T_1)$<br>$=0+0+1=1$<br><br>$T_1(\theta,\alpha^-,\alpha^+)$<br>$=(\theta)(T_1)\times 2^2+(\alpha^-)(T_1)\times 2+(\alpha^+)(T_1)$<br>$=0+2+1=3$<br><br>$T_1(\alpha^-,\alpha^+,\beta^-)$<br>$=(\alpha^-)(T_1)\times 2^2+(\alpha^+)(T_1)\times 2+(\beta^-)(T_1)$<br>$=4+2+0=6$<br><br>$T_1(\alpha^+,\beta^-,\beta^+)$<br>$=(\alpha^+)(T_1)\times 2^2+(\beta^-)(T_1)\times 2+(\beta^+)(T_1)$<br>$=4+0+0=4$<br><br>$T_1(\beta^-,\beta^+,\gamma^-)$<br>$=(\beta^-)(T_1)\times 2^2+(\beta^+)(T_1)\times 2+(\gamma^-)(T_1)$<br>$=0+0+0=0$<br><br>$T_1(\beta^+,\gamma^-,\gamma^+)$<br>$=(\beta^+)(T_1)\times 2^2+(\gamma^-)(T_1)\times 2+(\gamma^+)(T_1)$<br>$=0+0+0=0$ | $(\delta)(T_1,T_2,T_3)$<br>$=(\delta)(T_1)\times 2^2$<br>$+(\delta)(T_2)\times 2$<br>$+(\delta)(T_3)$<br>$=0+2+1=3$<br><br>$(\theta)(T_1,T_2,T_3)$<br>$=(\theta)(T_1)\times 2^2$<br>$+(\theta)(T_2)\times 2$<br>$+(\theta)(T_3)$<br>$=0+2+1=3$<br><br>$(\alpha^-)(T_1,T_2,T_3)$<br>$=(\alpha^-)(T_1)\times 2^2$<br>$+(\alpha^-)(T_2)\times 2$<br>$+(\alpha^-)(T_3)$<br>$=4+2+1=7$<br><br>$(\alpha^+)(T_1,T_2,T_3)$<br>$=(\alpha^+)(T_1)\times 2^2$<br>$+(\alpha^+)(T_2)\times 2$<br>$+(\alpha^+)(T_3)$<br>$=4+0+1=5$ | $(\beta^-)(T_1,T_2,T_3)$<br>$=(\beta^-)(T_1)\times 2^2$<br>$+(\beta^-)(T_2)\times 2$<br>$+(\beta^-)(T_3)$<br>$=0+2+0=2$<br><br>$(\beta^+)(T_1,T_2,T_3)$<br>$=(\beta^+)(T_1)\times 2^2$<br>$+(\beta^+)(T_2)\times 2$<br>$+(\beta^+)(T_3)$<br>$=0+2+1=3$<br><br>$(\gamma^-)(T_1,T_2,T_3)$<br>$=(\gamma^-)(T_1)\times 2^2$<br>$+(\gamma^-)(T_2)\times 2$<br>$+(\gamma^-)(T_3)$<br>$=0+2+1=3$<br><br>$(\gamma^+)(T_1,T_2,T_3)$<br>$=(\gamma^+)(T_1)\times 2^2$<br>$+(\gamma^+)(T_2)\times 2$<br>$+(\gamma^+)(T_3)$<br>$=0+2+0=2$ |

FIG. 8A

| | 1st note set | 2nd note set | 3rd note set | 4th note set |
|---|---|---|---|---|
| $T_1$ | | $T_1(\gamma^-,\gamma^+,\delta)$<br>$=(\gamma^-)(T_1)\times 2^2+(\gamma^+)(T_1)\times 2+(\delta)(T_1)$<br>$=0+0+0=0$<br><br>$T_1(\gamma^+,\delta^+,\theta)$<br>$=(\gamma^+)(T_1)\times 2^2+(\delta^+)(T_1)\times 2+(\theta)(T_1)$<br>$=0+0+0=0$ | | |
| $T_2$ | $(Att)(T_2,T_3,T_4)$<br>$=(Att)(T_2)\times 2^2$<br>$+(Att)(T_3)\times 2$<br>$+(Att)(T_4)$<br>$=4+0+0=4$<br><br>$(Med)(T_2,T_3,T_4)$<br>$=(Med)(T_2)\times 2^2$<br>$+(Med)(T_3)\times 2$<br>$+(Med)(T_4)$<br>$=0+2+1=3$ | $T_2(\delta,\theta,\alpha^-)$<br>$=(\delta)(T_2)\times 2^2+(\theta)(T_2)\times 2+(\alpha^-)(T_2)$<br>$=4+2+1=7$<br><br>$T_2(\theta,\alpha^-,\alpha^+)$<br>$=(\theta)(T_2)\times 2^2+(\alpha^-)(T_2)\times 2+(\alpha^+)(T_2)$<br>$=4+2+0=6$<br><br>$T_2(\alpha^-,\alpha^+,\beta^-)$<br>$=(\alpha^-)(T_2)\times 2^2+(\alpha^+)(T_2)\times 2+(\beta^-)(T_2)$<br>$=4+0+1=5$<br><br>$T_2(\alpha^+,\beta^-,\beta^+)$<br>$=(\alpha^+)(T_2)\times 2^2+(\beta^-)(T_2)\times 2+(\beta^+)(T_2)$<br>$=0+2+1=3$ | $(\delta)(T_2,T_3,T_4)$<br>$=(\delta)(T_2)\times 2^2$<br>$+(\delta)(T_3)\times 2$<br>$+(\delta)(T_4)$<br>$=4+2+0=6$<br><br>$(\theta)(T_2,T_3,T_4)$<br>$=(\theta)(T_2)\times 2^2$<br>$+(\theta)(T_3)\times 2$<br>$+(\theta)(T_4)$<br>$=4+2+1=7$<br><br>$(\alpha^-)(T_2,T_3,T_4)$<br>$=(\alpha^-)(T_2)\times 2^2$<br>$+(\alpha^-)(T_3)\times 2$<br>$+(\alpha^-)(T_4)$<br>$=4+2+0=6$ | $(\beta^-)(T_2,T_3,T_4)$<br>$=(\beta^-)(T_2)\times 2^2$<br>$+(\beta^-)(T_3)\times 2$<br>$+(\beta^-)(T_4)$<br>$=4+0+1=5$<br><br>$(\beta^+)(T_2,T_3,T_4)$<br>$=(\beta^+)(T_2)\times 2^2$<br>$+(\beta^+)(T_3)\times 2$<br>$+(\beta^+)(T_4)$<br>$=4+2+0=6$<br><br>$(\gamma^-)(T_2,T_3,T_4)$<br>$=(\gamma^-)(T_2)\times 2^2$<br>$+(\gamma^-)(T_3)\times 2$<br>$+(\gamma^-)(T_4)$<br>$=4+2+0=6$ |

FIG. 8B

|  | 1st note set | 2nd note set | 3rd note set | 4th note set |
|---|---|---|---|---|
| $T_2$ |  | $T_2(\beta^-,\beta^+,\gamma^-)$<br>$=(\beta^-)(T_2)\times2^2+(\beta^+)(T_2)\times2+(\gamma^-)(T_2)$<br>$=4+2+1=7$<br><br>$T_2(\beta^+,\gamma^-,\gamma^+)$<br>$=(\beta^+)(T_2)\times2^2+(\gamma^-)(T_2)\times2+(\gamma^+)(T_2)$<br>$=4+2+1=7$<br><br>$T_2(\gamma^-,\gamma^+,\delta)$<br>$=(\gamma^-)(T_2)\times2^2+(\gamma^+)(T_2)\times2+(\delta)(T_2)$<br>$=4+2+1=7$<br><br>$T_2(\gamma^+,\delta,\theta)$<br>$=(\gamma^+)(T_2)\times2^2+(\delta)(T_2)\times2+(\theta)(T_2)$<br>$=4+2+1=7$ | $(\alpha^+)(T_2,T_3,T_4)$<br>$=(\alpha^+)(T_2)\times2^2$<br>$+(\alpha^+)(T_3)\times2$<br>$+(\alpha^+)(T_4)$<br>$=0+2+0=2$ | $(\gamma^+)(T_2,T_3,T_4)$<br>$=(\gamma^+)(T_2)\times2^2$<br>$+(\gamma^+)(T_3)\times2$<br>$+(\gamma^+)(T_4)$<br>$=4+0+1=5$ |
| $T_3$ | $(Att)(T_3,T_4,T_5)$<br>$=(Att)(T_3)\times2^2$<br>$+(Att)(T_4)\times2$<br>$+(Att)(T_5)$<br>$=0+0+1=1$ | $T_3(\delta,\theta,\alpha^-)$<br>$=(\delta)(T_3)\times2^2+(\theta)(T_3)\times2+(\alpha^-)(T_3)$<br>$=4+2+1=7$<br><br>$T_3(\theta,\alpha^-,\alpha^+)$<br>$=(\theta)(T_3)\times2^2+(\alpha^-)(T_3)\times2+(\alpha^+)(T_3)$<br>$=4+2+1=7$ | $(\delta)(T_3,T_4,T_5)$<br>$=(\delta)(T_3)\times2^2$<br>$+(\delta)(T_4)\times2$<br>$+(\delta)(T_5)$<br>$=4+0+0=4$ | $(\beta^-)(T_3,T_4,T_5)$<br>$=(\beta^-)(T_3)\times2^2$<br>$+(\beta^-)(T_4)\times2$<br>$+(\beta^-)(T_5)$<br>$=0+2+0=2$ |

FIG. 8C

| | 1st note set | 2nd note set | 3rd note set | 4th note set |
|---|---|---|---|---|
| $T_3$ | $(Med)(T_3,T_4,T_5)$<br>$=(Med)(T_3) \times 2^2$<br>$+(Med)(T_4) \times 2$<br>$+(Med)(T_5)$<br>$=4+2+0=6$ | $T_3(\alpha^-,\alpha^+,\beta^-)$<br>$=(\alpha^-)(T_3) \times 2^2+(\alpha^+)(T_3) \times 2+(\beta^-)(T_3)$<br>$=4+2+0=6$<br><br>$T_3(\alpha^+,\beta^-,\beta^+)$<br>$=(\alpha^+)(T_3) \times 2^2+(\beta^-)(T_3) \times 2+(\beta^+)(T_3)$<br>$=4+0+1=5$<br><br>$T_3(\beta^-,\beta^+,\gamma^-)$<br>$=(\beta^-)(T_3) \times 2^2+(\beta^+)(T_3) \times 2+(\gamma^-)(T_3)$<br>$=0+2+1=3$<br><br>$T_3(\beta^+,\gamma^-,\gamma^+)$<br>$=(\beta^+)(T_3) \times 2^2+(\gamma^-)(T_3) \times 2+(\gamma^+)(T_3)$<br>$=4+2+0=6$<br><br>$T_3(\gamma^-,\gamma^+,\delta)$<br>$=(\gamma^-)(T_3) \times 2^2+(\gamma^+)(T_3) \times 2+(\delta)(T_3)$<br>$=4+0+1=5$<br><br>$T_3(\gamma^+,\delta,\theta)$<br>$=(\gamma^+)(T_3) \times 2^2+(\delta)(T_3) \times 2+(\theta)(T_3)$<br>$=0+2+1=3$ | $(\theta)(T_3,T_4,T_5)$<br>$=(\theta)(T_3) \times 2^2$<br>$+(\theta)(T_4) \times 2$<br>$+(\theta)(T_5)$<br>$=4+2+1=7$<br><br>$(\alpha^-)(T_3,T_4,T_5)$<br>$=(\alpha^-)(T_3) \times 2^2$<br>$+(\alpha^-)(T_4) \times 2$<br>$+(\alpha^-)(T_5)$<br>$=4+0+0=4$<br><br>$(\alpha^+)(T_3,T_4,T_5)$<br>$=(\alpha^+)(T_3) \times 2^2$<br>$+(\alpha^+)(T_4) \times 2$<br>$+(\alpha^+)(T_5)$<br>$=4+0+1=5$ | $(\beta^+)(T_3,T_4,T_5)$<br>$=(\beta^+)(T_3) \times 2^2$<br>$+(\beta^+)(T_4) \times 2$<br>$+(\beta^+)(T_5)$<br>$=4+0+1=5$<br><br>$(\gamma^-)(T_3,T_4,T_5)$<br>$=(\gamma^-)(T_3) \times 2^2$<br>$+(\gamma^-)(T_4) \times 2$<br>$+(\gamma^-)(T_5)$<br>$=4+0+0=4$<br><br>$(\gamma^+)(T_3,T_4,T_5)$<br>$=(\gamma^+)(T_3) \times 2^2$<br>$+(\gamma^+)(T_4) \times 2$<br>$+(\gamma^+)(T_5)$<br>$=0+2+0=2$ |

FIG. 8D

|  | 1st note set | 2nd note set | 3rd note set | 4th note set |
|---|---|---|---|---|
| $T_n$ | $(Att)(T_n, T_{n+1}, T_{n+2})$<br>$=(Att)(T_n) \times 2^2$<br>$+(Att)(T_{n+1}) \times 2$<br>$+(Att)(T_{n+2})$<br>$=4+2+0=6$ | $T_n(\delta, \theta, \alpha^-)$<br>$=(\delta)(T_n) \times 2^2 + (\theta)(T_n) \times 2 + (\alpha^-)(T_n)$ | $(\delta)(T_n, T_{n+1}, T_{n+2})$<br>$=(\delta)(T_n) \times 2^2$<br>$+(\delta)(T_{n+1}) \times 2$<br>$+(\delta)(T_{n+2})$ | $(\beta^-)(T_n, T_{n+1}, T_{n+2})$<br>$=(\beta^-)(T_n) \times 2^2$<br>$+(\beta^-)(T_{n+1}) \times 2$<br>$+(\beta^-)(T_{n+2})$ |
|  | $(Med)(T_n, T_{n+1}, T_{n+2})$<br>$=(Med)(T_n) \times 2^2$<br>$+(Med)(T_{n+1}) \times 2$<br>$+(Med)(T_{n+2})$<br>$=4+0+1=5$ | $T_n(\theta, \alpha^-, \alpha^+)$<br>$=(\theta)(T_n) \times 2^2 + (\alpha^-)(T_n) \times 2 + (\alpha^+)(T_n)$ | $(\theta)(T_n, T_{n+1}, T_{n+2})$<br>$=(\theta)(T_n) \times 2^2$<br>$+(\theta)(T_{n+1}) \times 2$<br>$+(\theta)(T_{n+2})$ | $(\beta^+)(T_n, T_{n+1}, T_{n+2})$<br>$=(\beta^+)(T_n) \times 2^2$<br>$+(\beta^+)(T_{n+1}) \times 2$<br>$+(\beta^+)(T_{n+2})$ |
|  |  | $T_n(\alpha^-, \alpha^+, \beta^-)$<br>$=(\alpha^-)(T_n) \times 2^2 + (\alpha^+)(T_n) \times 2 + (\beta^-)(T_n)$ | $(\alpha^-)(T_n, T_{n+1}, T_{n+2})$<br>$=(\alpha^-)(T_n) \times 2^2$<br>$+(\alpha^-)(T_{n+1}) \times 2$<br>$+(\alpha^-)(T_{n+2})$ | $(\gamma^-)(T_n, T_{n+1}, T_{n+2})$<br>$=(\gamma^-)(T_n) \times 2^2$<br>$+(\gamma^-)(T_{n+1}) \times 2$<br>$+(\gamma^-)(T_{n+2})$ |
|  |  | $T_n(\alpha^+, \beta^-, \beta^+)$<br>$=(\alpha^+)(T_n) \times 2^2 + (\beta^-)(T_n) \times 2 + (\beta^+)(T_n)$ |  |  |
|  |  | $T_n(\beta^-, \beta^+, \gamma^-)$<br>$=(\beta^-)(T_n) \times 2^2 + (\beta^+)(T_n) \times 2 + (\gamma^-)(T_n)$ | $(\alpha^+)(T_n, T_{n+1}, T_{n+2})$<br>$=(\alpha^+)(T_n) \times 2^2$<br>$+(\alpha^+)(T_{n+1}) \times 2$<br>$+(\alpha^+)(T_{n+2})$ | $(\gamma^+)(T_n, T_{n+1}, T_{n+2})$<br>$=(\gamma^+)(T_n) \times 2^2$<br>$+(\gamma^+)(T_{n+1}) \times 2$<br>$+(\gamma^+)(T_{n+2})$ |
|  |  | $T_n(\beta^+, \gamma^-, \gamma^+)$<br>$=(\beta^+)(T_n) \times 2^2 + (\gamma^-)(T_n) \times 2 + (\gamma^+)(T_n)$ |  |  |
|  |  | $T_n(\gamma^-, \gamma^+, \delta)$<br>$=(\gamma^-)(T_n) \times 2^2 + (\gamma^+)(T_n) \times 2 + (\delta)(T_n)$ |  |  |
|  |  | $T_n(\gamma^+, \delta^+, \theta)$<br>$=(\gamma^+)(T_n) \times 2^2 + (\delta^+)(T_n) \times 2 + (\theta)(T_n)$ |  |  |

FIG. 8E

|   | 1st note set | 2nd note set | 3rd note set | 4th note set |
|---|---|---|---|---|
| $T_1$ | $T_1(\delta, \theta, \alpha^-)$<br>$=(\delta)(T_1) \times 2^2 + (\theta)(T_1) \times 2$<br>$+(\alpha^-)(T_1)$<br>$=0+0+1=1$ | $T_1(\beta^-, \beta^+, \gamma^-)$<br>$=(\beta^-)(T_1) \times 2^2 + (\beta^+)(T_1) \times 2$<br>$+(\gamma^-)(T_1)$<br>$=0+0+0=0$ | $(\delta)(T_1, T_2, T_3)$<br>$=(\delta)(T_1) \times 2^2 + (\delta)(T_2) \times 2$<br>$+(\delta)(T_3)$<br>$=0+2+1=3$ | $(\beta^-)(T_1, T_2, T_3)$<br>$=(\beta^-)(T_1) \times 2^2 + (\beta^-)(T_2) \times 2$<br>$+(\beta^-)(T_3)$<br>$=0+2+0=2$ |
|   | $T_1(\theta, \alpha^-, \alpha^+)$<br>$=(\theta)(T_1) \times 2^2 + (\alpha^-)(T_1) \times 2$<br>$+(\alpha^+)(T_1)$<br>$=0+2+1=3$ | $T_1(\beta^+, \gamma^-, \gamma^+)$<br>$=(\beta^+)(T_1) \times 2^2 + (\gamma^-)(T_1) \times 2$<br>$+(\gamma^+)(T_1)$<br>$=0+0+0=0$ | $(\theta)(T_1, T_2, T_3)$<br>$=(\theta)(T_1) \times 2^2 + (\theta)(T_2) \times 2$<br>$+(\theta)(T_3)$<br>$=0+2+1=3$ | $(\beta^+)(T_1, T_2, T_3)$<br>$=(\beta^+)(T_1) \times 2^2 + (\beta^+)(T_2) \times 2$<br>$+(\beta^+)(T_3)$<br>$=0+2+1=3$ |
|   | $T_1(\alpha^-, \alpha^+, \beta^-)$<br>$=(\alpha^-)(T_1) \times 2^2 + (\alpha^+)(T_1) \times 2$<br>$+(\beta^-)(T_1)$<br>$=4+2+0=6$ | $T_1(\gamma^-, \gamma^+, \delta)$<br>$=(\gamma^-)(T_1) \times 2^2 + (\gamma^+)(T_1) \times 2$<br>$+(\delta)(T_1)$<br>$=0+0+0=0$ | $(\alpha^-)(T_1, T_2, T_3)$<br>$=(\alpha^-)(T_1) \times 2^2 + (\alpha^-)(T_2) \times 2$<br>$+(\alpha^-)(T_3)$<br>$=4+2+1=7$ | $(\gamma^-)(T_1, T_2, T_3)$<br>$=(\gamma^-)(T_1) \times 2^2 + (\gamma^-)(T_2) \times 2$<br>$+(\gamma^-)(T_3)$<br>$=0+2+1=3$ |
|   | $T_1(\alpha^+, \beta^-, \beta^+)$<br>$=(\alpha^+)(T_1) \times 2^2 + (\beta^-)(T_1) \times 2$<br>$+(\beta^+)(T_1)$<br>$=4+0+0=4$ | $T_1(\gamma^+, \delta, \theta)$<br>$=(\gamma^+)(T_1) \times 2^2 + (\delta)(T_1) \times 2$<br>$+(\theta)(T_1)$<br>$=0+0+0=0$ | $(\alpha^+)(T_1, T_2, T_3)$<br>$=(\alpha^+)(T_1) \times 2^2 + (\alpha^+)(T_2) \times 2$<br>$+(\alpha^+)(T_3)$<br>$=4+0+1=5$ | $(\gamma^+)(T_1, T_2, T_3)$<br>$=(\gamma^+)(T_1) \times 2^2 + (\gamma^+)(T_2) \times 2$<br>$+(\gamma^+)(T_3)$<br>$=0+2+0=2$ |
| $T_2$ | $T_2(\delta, \theta, \alpha^-)$<br>$=(\delta)(T_2) \times 2^2 + (\theta)(T_2) \times 2$<br>$+(\alpha^-)(T_2)$<br>$=4+2+1=7$ | $T_2(\beta^-, \beta^+, \gamma^-)$<br>$=(\beta^-)(T_2) \times 2^2 + (\beta^+)(T_2) \times 2$<br>$+(\gamma^-)(T_2)$<br>$=4+2+1=7$ | $(\delta)(T_2, T_3, T_4)$<br>$=(\delta)(T_2) \times 2^2 + (\delta)(T_3) \times 2$<br>$+(\delta)(T_4)$<br>$=4+2+0=6$ | $(\beta^-)(T_2, T_3, T_4)$<br>$=(\beta^-)(T_2) \times 2^2 + (\beta^-)(T_3) \times 2$<br>$+(\beta^-)(T_4)$<br>$=4+0+1=5$ |

FIG. 9A

|  | 1st note set | 2nd note set | 3rd note set | 4th note set |
|---|---|---|---|---|
| $T_2$ | $T_2(\theta, \alpha^-, \alpha^+)$<br>$=(\theta)(T_2)\times 2^2+(\alpha^-)(T_2)\times 2$<br>$+(\alpha^+)(T_2)$<br>$=4+2+0=6$ | $T_2(\beta^+, \gamma^-, \gamma^+)$<br>$=(\beta^+)(T_2)\times 2^2+(\gamma^-)(T_2)\times 2$<br>$+(\gamma^+)(T_2)$<br>$=4+2+1=7$ | $(\theta)(T_2,T_3,T_4)$<br>$=(\theta)(T_2)\times 2^2+(\theta)(T_3)\times 2$<br>$+(\theta)(T_4)$<br>$=4+2+1=7$ | $(\beta^+)(T_2,T_3,T_4)$<br>$=(\beta^+)(T_2)\times 2^2+(\beta^+)(T_3)\times 2$<br>$+(\beta^+)(T_4)$<br>$=4+2+0=6$ |
|  | $T_2(\alpha^-, \alpha^+, \beta^-)$<br>$=(\alpha^-)(T_2)\times 2^2+(\alpha^+)(T_2)\times 2$<br>$+(\beta^-)(T_2)$<br>$=4+0+1=5$ | $T_2(\gamma^-, \gamma^+, \delta)$<br>$=(\gamma^-)(T_2)\times 2^2+(\gamma^+)(T_2)\times 2$<br>$+(\delta)(T_2)$<br>$=4+2+1=7$ | $(\alpha^-)(T_2,T_3,T_4)$<br>$=(\alpha^-)(T_2)\times 2^2+(\alpha^-)(T_3)\times 2$<br>$+(\alpha^-)(T_4)$<br>$=4+2+0=6$ | $(\gamma^-)(T_2,T_3,T_4)$<br>$=(\gamma^-)(T_2)\times 2^2+(\gamma^-)(T_3)\times 2$<br>$+(\gamma^-)(T_4)$<br>$=4+2+0=6$ |
|  | $T_2(\alpha^+, \beta^-, \beta^+)$<br>$=(\alpha^+)(T_2)\times 2^2+(\beta^-)(T_2)\times 2$<br>$+(\beta^+)(T_2)$<br>$=0+2+1=3$ | $T_2(\gamma^+, \delta, \theta)$<br>$=(\gamma^+)(T_2)\times 2^2+(\delta)(T_2)\times 2$<br>$+(\theta)(T_2)$<br>$=4+2+1=7$ | $(\alpha^+)(T_2,T_3,T_4)$<br>$=(\alpha^+)(T_2)\times 2^2+(\alpha^+)(T_3)\times 2$<br>$+(\alpha^+)(T_4)$<br>$=0+2+0=2$ | $(\gamma^+)(T_2,T_3,T_4)$<br>$=(\gamma^+)(T_2)\times 2^2+(\gamma^+)(T_3)\times 2$<br>$+(\gamma^+)(T_4)$<br>$=4+0+1=5$ |
| $T_3$ | $T_3(\delta, \theta, \alpha^-)$<br>$=(\delta)(T_3)\times 2^2+(\theta)(T_3)\times 2$<br>$+(\alpha^-)(T_3)$<br>$=4+2+1=7$ | $T_3(\beta^-, \beta^+, \gamma^-)$<br>$=(\beta^-)(T_3)\times 2^2+(\beta^+)(T_3)\times 2$<br>$+(\gamma^-)(T_3)$<br>$=0+2+1=3$ | $(\delta)(T_3,T_4,T_5)$<br>$=(\delta)(T_3)\times 2^2+(\delta)(T_4)\times 2$<br>$+(\delta)(T_5)$<br>$=4+0+0=4$ | $(\beta^-)(T_3,T_4,T_5)$<br>$=(\beta^-)(T_3)\times 2^2+(\beta^-)(T_4)\times 2$<br>$+(\beta^-)(T_5)$<br>$=0+2+0=2$ |
|  | $T_3(\theta, \alpha^-, \alpha^+)$<br>$=(\theta)(T_3)\times 2^2+(\alpha^-)(T_3)\times 2$<br>$+(\alpha^+)(T_3)$<br>$=4+2+1=7$ | $T_3(\beta^+, \gamma^-, \gamma^+)$<br>$=(\beta^+)(T_3)\times 2^2+(\gamma^-)(T_3)\times 2$<br>$+(\gamma^+)(T_3)$<br>$=4+2+0=6$ | $(\theta)(T_3,T_4,T_5)$<br>$=(\theta)(T_3)\times 2^2+(\theta)(T_4)\times 2$<br>$+(\theta)(T_5)$<br>$=4+2+1=7$ | $(\beta^+)(T_3,T_4,T_5)$<br>$=(\beta^+)(T_3)\times 2^2+(\beta^+)(T_4)\times 2$<br>$+(\beta^+)(T_5)$<br>$=4+0+1=5$ |

FIG. 9B

|   | 1st note set | 2nd note set | 3rd note set | 4th note set |
|---|---|---|---|---|
| $T_3$ | $T_3(\alpha^-,\alpha^+,\beta^-)$<br>$=(\alpha^-)(T_3)\times 2^2+(\alpha^+)(T_3)\times 2$<br>$+(\beta^-)(T_3)$<br>$=4+2+0=6$ | $T_3(\gamma^-,\gamma^+,\delta)$<br>$=(\gamma^-)(T_3)\times 2^2+(\gamma^+)(T_3)\times 2$<br>$+(\delta)(T_3)$<br>$=4+0+1=5$ | $(\alpha^-)(T_3,T_4,T_5)$<br>$=(\alpha^-)(T_3)\times 2^2+(\alpha^-)(T_4)\times 2$<br>$+(\alpha^-)(T_5)$<br>$=4+0+0=4$ | $(\gamma^-)(T_3,T_4,T_5)$<br>$=(\gamma^-)(T_3)\times 2^2+(\gamma^-)(T_4)\times 2$<br>$+(\gamma^-)(T_5)$<br>$=4+0+0=4$ |
|   | $T_3(\alpha^+,\beta^-,\beta^+)$<br>$=(\alpha^+)(T_3)\times 2^2+(\beta^-)(T_3)\times 2$<br>$+(\beta^+)(T_3)$<br>$=4+0+1=5$ | $T_3(\gamma^+,\delta,\theta)$<br>$=(\gamma^+)(T_3)\times 2^2+(\delta)(T_3)\times 2$<br>$+(\theta)(T_3)$<br>$=0+2+1=3$ | $(\alpha^+)(T_3,T_4,T_5)$<br>$=(\alpha^+)(T_3)\times 2^2+(\alpha^+)(T_4)\times 2$<br>$+(\alpha^+)(T_5)$<br>$=4+0+1=5$ | $(\gamma^+)(T_3,T_4,T_5)$<br>$=(\gamma^+)(T_3)\times 2^2+(\gamma^+)(T_4)\times 2$<br>$+(\gamma^+)(T_5)$<br>$=0+2+0=2$ |
| $T_n$ | $T_n(\delta,\theta,\alpha^-)$<br>$=(\delta)(T_n)\times 2^2+(\theta)(T_n)\times 2$<br>$+(\alpha^-)(T_n)$ | $T_n(\beta^-,\beta^+,\gamma^-)$<br>$=(\beta^-)(T_n)\times 2^2+(\beta^+)(T_n)\times 2$<br>$+(\gamma^-)(T_n)$ | $(\delta)(T_n,T_{n+1},T_{n+2})$<br>$=(\delta)(T_n)\times 2^2+(\delta)(T_{n+1})\times 2$<br>$+(\delta)(T_{n+2})$ | $(\beta^-)(T_n,T_{n+1},T_{n+2})$<br>$=(\beta^-)(T_n)\times 2^2+(\beta^-)(T_{n+1})\times 2$<br>$+(\beta^-)(T_{n+2})$ |
|   | $T_n(\theta,\alpha^-,\alpha^+)$<br>$=(\theta)(T_n)\times 2^2+(\alpha^-)(T_n)\times 2$<br>$+(\alpha^+)(T_n)$ | $T_n(\beta^+,\gamma^-,\gamma^+)$<br>$=(\beta^+)(T_n)\times 2^2+(\gamma^-)(T_n)\times 2$<br>$+(\gamma^+)(T_n)$ | $(\theta)(T_n,T_{n+1},T_{n+2})$<br>$=(\theta)(T_n)\times 2^2+(\theta)(T_{n+1})\times 2$<br>$+(\theta)(T_{n+2})$ | $(\beta^+)(T_n,T_{n+1},T_{n+2})$<br>$=(\beta^+)(T_n)\times 2^2+(\beta^+)(T_{n+1})\times 2$<br>$+(\beta^+)(T_{n+2})$ |
|   | $T_n(\alpha^-,\alpha^+,\beta^-)$<br>$=(\alpha^-)(T_n)\times 2^2+(\alpha^+)(T_n)\times 2$<br>$+(\beta^-)(T_n)$ | $T_n(\gamma^-,\gamma^+,\delta)$<br>$=(\gamma^-)(T_n)\times 2^2+(\gamma^+)(T_n)\times 2$<br>$+(\delta)(T_n)$ | $(\alpha^-)(T_n,T_{n+1},T_{n+2})$<br>$=(\alpha^-)(T_n)\times 2^2+(\alpha^-)(T_{n+1})\times 2$<br>$+(\alpha^-)(T_{n+2})$ | $(\gamma^-)(T_n,T_{n+1},T_{n+2})$<br>$=(\gamma^-)(T_n)\times 2^2+(\gamma^-)(T_{n+1})\times 2$<br>$+(\gamma^-)(T_{n+2})$ |
|   | $T_n(\alpha^+,\beta^-,\beta^+)$<br>$=(\alpha^+)(T_n)\times 2^2+(\beta^-)(T_n)\times 2$<br>$+(\beta^+)(T_n)$ | $T_n(\gamma^+,\delta,\theta)$<br>$=(\gamma^+)(T_n)\times 2^2+(\delta)(T_n)\times 2$<br>$+(\theta)(T_n)$ | $(\alpha^+)(T_n,T_{n+1},T_{n+2})$<br>$=(\alpha^+)(T_n)\times 2^2+(\alpha^+)(T_{n+1})\times 2$<br>$+(\alpha^+)(T_{n+2})$ | $(\gamma^+)(T_n,T_{n+1},T_{n+2})$<br>$=(\gamma^+)(T_n)\times 2^2+(\gamma^+)(T_{n+1})\times 2$<br>$+(\gamma^+)(T_{n+2})$ |

FIG. 9C

| | Not conversion rule | Beats |
|---|---|---|
| $T_1$ | $(Att)(T_1,T_2,T_3)$<br>$=(Att)(T_1)\times 2^2+(Att)(T_2)\times 2+(Att)(T_3)$<br>$=4+2+0=6$ | $(Med)(T_1,T_2)$<br>$=(Med)(T_1)\times 2+(Med)(T_2)$<br>$=2+0=2$ |
| | $(Med)(T_1,T_2,T_3)$<br>$=(Med)(T_1)\times 2^2+(Med)(T_2)\times 2+(Med)(T_3)$<br>$=4+0+1=5$ | $(Att)(T_1,T_2)$<br>$=(Att)(T_1)\times 2+(Att)(T_2)$<br>$=2+1=3$ |
| | $T_1(\delta,\theta,\alpha^-)$<br>$=(\delta)(T_1)\times 2^2+(\theta)(T_1)\times 2+(\alpha^-)(T_1)$<br>$=0+2+1=3$ | $T_1(\alpha^+,\beta^-)$<br>$=(\alpha^+)(T_1)\times 2+(\beta^-)(T_1)$<br>$=2+0=2$ |
| | $T_1(\theta,\alpha^-,\alpha^+)$<br>$=(\theta)(T_1)\times 2^2+(\alpha^-)(T_1)\times 2+(\alpha^+)(T_1)$<br>$=0+2+1=3$ | $T_1(\beta^-,\beta^+)$<br>$=(\beta^-)(T_1)\times 2+(\beta^+)(T_1)$<br>$=0+0=0$ |
| | $T_1(\alpha^-,\alpha^+,\beta^-)$<br>$=(\alpha^-)(T_1)\times 2^2+(\alpha^+)(T_1)\times 2+(\beta^-)(T_1)$<br>$=4+2+0=6$ | $T_1(\beta^+,\gamma^-)$<br>$=(\beta^+)(T_1)\times 2+(\gamma^-)(T_1)$<br>$=0+0=0$ |
| | $T_1(\alpha^+,\beta^-,\beta^+)$<br>$=(\alpha^+)(T_1)\times 2^2+(\beta^-)(T_1)\times 2+(\beta^+)(T_1)$<br>$=4+0+0=4$ | $T_1(\gamma^-,\gamma^+)$<br>$=(\gamma^-)(T_1)\times 2+(\gamma^+)(T_1)$<br>$=0+0=0$ |
| | $T_1(\beta^-,\beta^+,\gamma^-)$<br>$=(\beta^-)(T_1)\times 2^2+(\beta^+)(T_1)\times 2+(\gamma^-)(T_1)$<br>$=0+0+0=0$ | $T_1(\gamma^+,\delta)$<br>$=(\gamma^+)(T_1)\times 2+(\delta)(T_1)$<br>$=0+0=0$ |
| | $T_1(\beta^+,\gamma^-,\gamma^+)$<br>$=(\beta^+)(T_1)\times 2^2+(\gamma^-)(T_1)\times 2+(\gamma^+)(T_1)$<br>$=0+0+0=0$ | $T_1(\delta,\theta)$<br>$=(\delta)(T_1)\times 2+(\theta)(T_1)$<br>$=0+0=0$ |

FIG. 10A

| | Not conversion rule | Beats |
|---|---|---|
| $T_1$ | $T_1(\gamma^-, \gamma^+, \delta)$<br>$=(\gamma^-)(T_1)\times 2^2+(\gamma^+)(T_1)\times 2+(\delta)(T_1)$<br>$=0+0+0=0$ | $T_1(\theta, \alpha^-)$<br>$=(\theta)(T_1)\times 2+(\alpha^-)(T_1)$<br>$=0+1=1$ |
| | $T_1(\gamma^+, \delta, \theta)$<br>$=(\gamma^+)(T_1)\times 2^2+(\delta)(T_1)\times 2+(\theta)(T_1)$<br>$=0+0+0=0$ | $T_1(\alpha^-, \alpha^+)$<br>$=(\alpha^-)(T_1)\times 2+(\alpha^+)(T_1)$<br>$=2+1=3$ |
| | $\delta(T_1, T_2, T_3)$<br>$=\delta(T_1)\times 2^2+\delta(T_2)\times 2+\delta(T_3)$<br>$=0+2+1=3$ | $\theta(T_1, T_2)$<br>$=\theta(T_1)\times 2+\theta(T_2)$<br>$=0+1=1$ |
| | $\theta(T_1, T_2, T_3)$<br>$=\theta(T_1)\times 2^2+\theta(T_2)\times 2+\theta(T_3)$<br>$=0+2+1=3$ | $\delta(T_1, T_2)$<br>$=\delta(T_1)\times 2+\delta(T_2)$<br>$=0+1=1$ |
| | $(\alpha^-)(T_1, T_2, T_3)$<br>$=(\alpha^-)(T_1)\times 2^2+(\alpha^-)(T_2)\times 2+(\alpha^-)(T_3)$<br>$=4+2+1=7$ | $(\alpha^+)(T_1, T_2)$<br>$=(\alpha^+)(T_1)\times 2+(\alpha^+)(T_2)$<br>$=2+0=2$ |
| | $(\alpha^+)(T_1, T_2, T_3)$<br>$=(\alpha^+)(T_1)\times 2^2+(\alpha^+)(T_2)\times 2+(\alpha^+)(T_3)$<br>$=4+0+1=5$ | $(\alpha^-)(T_1, T_2)$<br>$=(\alpha^-)(T_1)\times 2+(\alpha^-)(T_2)$<br>$=2+1=3$ |
| | $(\beta^-)(T_1, T_2, T_3)$<br>$=(\beta^-)(T_1)\times 2^2+(\beta^-)(T_2)\times 2+(\beta^-)(T_3)$<br>$=0+2+0=2$ | $(\beta^-)(T_1, T_2)$<br>$=(\beta^-)(T_1)\times 2+(\beta^+)(T_2)$<br>$=0+1=1$ |
| | $(\beta^+)(T_1, T_2, T_3)$<br>$=(\beta^+)(T_1)\times 2^2+(\beta^+)(T_2)\times 2+(\beta^+)(T_3)$<br>$=0+2+1=3$ | $(\beta^-)(T_1, T_2)$<br>$=(\beta^-)(T_1)\times 2+(\beta^-)(T_2)$<br>$=0+1=1$ |

FIG. 10B

|   | Not conversion rule | Beats |
|---|---|---|
| $T_1$ | $(\gamma^-)(T_1, T_2, T_3)$<br>$=(\gamma^-)(T_1) \times 2^2 + (\gamma^-)(T_2) \times 2 + (\gamma^-)(T_3)$<br>$=0+2+1=3$ | $(\gamma^+)(T_1, T_2)$<br>$=(\gamma^+)(T_1) \times 2 + (\gamma^+)(T_2)$<br>$=0+1=1$ |
| | $(\gamma^+)(T_1, T_2, T_3)$<br>$=(\gamma^+)(T_1) \times 2^2 + (\gamma^+)(T_2) \times 2 + (\gamma^+)(T_3)$<br>$=0+2+0=2$ | $(\gamma^-)(T_1, T_2)$<br>$=(\gamma^-)(T_1) \times 2 + (\gamma^-)(T_2)$<br>$=0+1=1$ |
| $T_2$ | $(Att)(T_2, T_3, T_4)$<br>$=(Att)(T_2) \times 2^2 + (Att)(T_3) \times 2 + (Att)(T_4)$<br>$=4+0+0=4$ | $(Med)(T_2, T_3)$<br>$=(Med)(T_2) \times 2 + (Med)(T_3)$<br>$=0+1=1$ |
| | $(Med)(T_2, T_3, T_4)$<br>$=(Med)(T_2) \times 2^2 + (Med)(T_3) \times 2 + (Med)(T_4)$<br>$=0+2+1=3$ | $(Att)(T_2, T_3)$<br>$=(Att)(T_2) \times 2 + (Att)(T_3)$<br>$=2+0=2$ |
| | $T_2(\delta, \theta, \alpha^-)$<br>$=(\delta)(T_2) \times 2^2 + (\theta)(T_2) \times 2 + (\alpha^-)(T_2)$<br>$=4+2+1=7$ | $T_2(\alpha^+, \beta^-)$<br>$=(\alpha^+)(T_2) \times 2 + (\beta^-)(T_2)$<br>$=0+1=1$ |
| | $T_2(\theta, \alpha^-, \alpha^+)$<br>$=(\theta)(T_2) \times 2^2 + (\alpha^-)(T_2) \times 2 + (\alpha^+)(T_2)$<br>$=4+2+0=6$ | $T_2(\beta^-, \beta^+)$<br>$=(\beta^-)(T_2) \times 2 + (\beta^+)(T_2)$<br>$=2+1=3$ |
| | $T_2(\alpha^-, \alpha^+, \beta^-)$<br>$=(\alpha^-)(T_2) \times 2^2 + (\alpha^+)(T_2) \times 2 + (\beta^-)(T_2)$<br>$=4+0+1=5$ | $T_2(\beta^+, \gamma^-)$<br>$=(\beta^+)(T_2) \times 2 + (\gamma^-)(T_2)$<br>$=2+1=3$ |
| | $T_2(\alpha^+, \beta^-, \beta^+)$<br>$=(\alpha^+)(T_2) \times 2^2 + (\beta^-)(T_2) \times 2 + (\beta^+)(T_2)$<br>$=0+2+1=3$ | $T_2(\gamma^-, \gamma^+)$<br>$=(\gamma^-)(T_2) \times 2 + (\gamma^+)(T_2)$<br>$=2+1=3$ |

FIG. 10C

| | Not conversion rule | Beats |
|---|---|---|
| $T_2$ | $T_2(\beta^-,\beta^+,\gamma^-)$<br>$=(\beta^-)(T_2)\times 2^2+(\beta^+)(T_2)\times 2+(\gamma^-)(T_2)$<br>$=4+2+1=7$ | $T_2(\gamma^+,\delta)$<br>$=(\gamma^+)(T_2)\times 2+(\delta)(T_2)$<br>$=2+1=3$ |
| | $T_2(\beta^+,\gamma^-,\gamma^+)$<br>$=(\beta^+)(T_2)\times 2^2+(\gamma^-)(T_2)\times 2+(\gamma^+)(T_2)$<br>$=4+2+1=7$ | $T_2(\delta,\theta)$<br>$=(\delta)(T_2)\times 2+(\theta)(T_2)$<br>$=2+1=3$ |
| | $T_2(\gamma^-,\gamma^+,\delta)$<br>$=(\gamma^-)(T_2)\times 2^2+(\gamma^+)(T_2)\times 2+(\delta)(T_2)$<br>$=4+2+1=7$ | $T_2(\theta,\alpha^-)$<br>$=(\theta)(T_2)\times 2+(\alpha^-)(T_2)$<br>$=2+1=3$ |
| | $T_2(\gamma^+,\delta,\theta)$<br>$=(\gamma^+)(T_2)\times 2^2+(\delta)(T_2)\times 2+(\theta)(T_2)$<br>$=4+2+1=7$ | $T_2(\alpha^-,\alpha^+)$<br>$=(\alpha^-)(T_2)\times 2+(\alpha^+)(T_2)$<br>$=2+0=2$ |
| | $\delta(T_2,T_3,T_4)$<br>$=\delta(T_2)\times 2^2+\delta(T_3)\times 2+\delta(T_4)$<br>$=4+2+0=6$ | $\theta(T_2,T_3)$<br>$=\theta(T_2)\times 2+\theta(T_3)$<br>$=2+1=3$ |
| | $\theta(T_2,T_3,T_4)$<br>$=\theta(T_2)\times 2^2+\theta(T_3)\times 2+\theta(T_4)$<br>$=4+2+0=6$ | $\delta(T_2,T_3)$<br>$=\delta(T_2)\times 2+\delta(T_3)$<br>$=2+1=3$ |
| | $(\alpha^-)(T_2,T_3,T_4)$<br>$=(\alpha^-)(T_2)\times 2^2+(\alpha^-)(T_3)\times 2+(\alpha^-)(T_4)$<br>$=4+2+0=6$ | $(\alpha^+)(T_2,T_3)$<br>$=(\alpha^+)(T_2)\times 2+(\alpha^+)(T_3)$<br>$=0+1=1$ |
| | $(\alpha^+)(T_2,T_3,T_4)$<br>$=(\alpha^+)(T_2)\times 2^2+(\alpha^+)(T_3)\times 2+(\alpha^+)(T_4)$<br>$=0+2+0=2$ | $(\alpha^-)(T_2,T_3)$<br>$=(\alpha^-)(T_2)\times 2+(\alpha^-)(T_3)$<br>$=2+1=3$ |

FIG. 10D

| | Not conversion rule | Beats |
|---|---|---|
| $T_2$ | $(\beta^-)(T_2,T_3,T_4)$<br>$=(\beta^-)(T_2)\times 2^2+(\beta^-)(T_3)\times 2+(\beta^-)(T_4)$<br>$=4+0+1=5$ | $(\beta^+)(T_2,T_3)$<br>$=(\beta^+)(T_2)\times 2+(\beta^+)(T_3)$<br>$=2+1=3$ |
| | $(\beta^+)(T_2,T_3,T_4)$<br>$=(\beta^+)(T_2)\times 2^2+(\beta^+)(T_3)\times 2+(\beta^+)(T_4)$<br>$=4+2+0=6$ | $(\beta^-)(T_2,T_3)$<br>$=(\beta^-)(T_2)\times 2+(\beta^-)(T_3)$<br>$=2+0=2$ |
| | $(\gamma^-)(T_2,T_3,T_4)$<br>$=(\gamma^-)(T_2)\times 2^2+(\gamma^-)(T_3)\times 2+(\gamma^-)(T_4)$<br>$=4+2+0=6$ | $(\gamma^+)(T_2,T_3)$<br>$=(\gamma^+)(T_2)\times 2+(\gamma^+)(T_3)$<br>$=2+0=2$ |
| | $(\gamma^+)(T_2,T_3,T_4)$<br>$=(\gamma^+)(T_2)\times 2^2+(\gamma^+)(T_3)\times 2+(\gamma^+)(T_4)$<br>$=4+0+1=5$ | $(\gamma^-)(T_2,T_3)$<br>$=(\gamma^-)(T_2)\times 2+(\gamma^-)(T_3)$<br>$=2+1=3$ |
| $T_n$ | $(Att)(T_n,T_{n+1},T_{n+2})$<br>$=(Att)(T_n)\times 2^2+(Att)(T_{n+1})\times 2+(Att)(T_{n+2})$ | $(Med)(T_n,T_{n+1})$<br>$=(Med)(T_n)\times 2+(Med)(T_{n+1})$ |
| | $(Med)(T_n,T_{n+1},T_{n+2})$<br>$=(Med)(T_n)\times 2^2+(Med)(T_{n+1})\times 2+(Med)(T_{n+2})$ | $(Att)(T_n,T_{n+1})$<br>$=(Att)(T_n)\times 2+(Att)(T_{n+1})$ |
| | $T_n(\delta,\theta,\alpha^-)$<br>$=(\delta)(T_n)\times 2^2+(\theta)(T_n)\times 2+(\alpha^-)(T_n)$ | $T_n(\alpha^+,\beta^-)$<br>$=(\alpha^+)(T_n)\times 2+(\beta^-)(T_n)$ |
| | $T_n(\theta,\alpha^-,\alpha^+)$<br>$=(\theta)(T_n)\times 2^2+(\alpha^-)(T_n)\times 2+(\alpha^+)(T_n)$ | $T_n(\beta^-,\beta^+)$<br>$=(\beta^-)(T_n)\times 2+(\beta^+)(T_n)$ |
| | $T_n(\alpha^-,\alpha^+,\beta^-)$<br>$=(\alpha^-)(T_n)\times 2^2+(\alpha^+)(T_n)\times 2+(\beta^-)(T_n)$ | $T_n(\beta^+,\gamma^-)$<br>$=(\beta^+)(T_n)\times 2+(\gamma^-)(T_n)$ |
| | $T_n(\alpha^+,\beta^-,\beta^+)$<br>$=(\alpha^+)(T_n)\times 2^2+(\beta^-)(T_n)\times 2+(\beta^+)(T_n)$ | $T_n(\gamma^-,\gamma^+)$<br>$=(\gamma^-)(T_n)\times 2+(\gamma^+)(T_n)$ |

FIG. 10E

| | Not conversion rule | Beats |
|---|---|---|
| $T_n$ | $T_n(\beta^-, \beta^+, \gamma^-)$<br>$=(\beta^-)(T_n) \times 2^2+(\beta^+)(T_n) \times 2+(\gamma^-)(T_n)$ | $T_n(\gamma^+, \delta)$<br>$=(\gamma^+)(T_n) \times 2+(\delta)(T_n)$ |
| | $T_n(\beta^+, \gamma^-, \gamma^+)$<br>$=(\beta^+)(T_n) \times 2^2+(\gamma^-)(T_n) \times 2+(\gamma^+)(T_n)$ | $T_n(\delta, \theta)$<br>$=(\delta)(T_n) \times 2+(\theta)(T_n)$ |
| | $T_n(\gamma^-, \gamma^+, \delta)$<br>$=(\gamma^-)(T_n) \times 2^2+(\gamma^+)(T_n) \times 2+(\delta)(T_n)$ | $T_n(\theta, \alpha^-)$<br>$=(\theta)(T_n) \times 2+(\alpha^-)(T_n)$ |
| | $T_n(\gamma^+, \delta, \theta)$<br>$=(\gamma^+)(T_n) \times 2^2+(\delta)(T_n) \times 2+(\theta)(T_n)$ | $T_n(\alpha^-, \alpha^+)$<br>$=(\alpha^-)(T_n) \times 2+(\alpha^+)(T_n)$ |
| | $\delta(T_n, T_{n+1}, T_{n+2})$<br>$=\delta(T_n) \times 2^2+\delta(T_{n+1}) \times 2+\delta(T_{n+2})$ | $\theta(T_n, T_{n+1})$<br>$=\delta(T_n) \times 2+\delta(T_{n+1})$ |
| | $\theta(T_n, T_{n+1}, T_{n+2})$<br>$=\theta(T_n) \times 2^2+\theta(T_{n+1}) \times 2+\theta(T_{n+2})$ | $\delta(T_n, T_{n+1})$<br>$=\theta(T_n) \times 2+\theta(T_{n+1})$ |
| | $(\alpha^-)(T_n, T_{n+1}, T_{n+2})$<br>$=(\alpha^-)(T_n) \times 2^2+(\alpha^-)(T_{n+1}) \times 2+(\alpha^-)(T_{n+2})$ | $(\alpha^+)(T_n, T_{n+1})$<br>$=(\alpha^-)(T_n) \times 2+(\alpha^+)(T_{n+1})$ |
| | $(\alpha^+)(T_n, T_{n+1}, T_{n+2})$<br>$=(\alpha^+)(T_n) \times 2^2+(\alpha^+)(T_{n+1}) \times 2+(\alpha^+)(T_{n+2})$ | $(\alpha^-)(T_n, T_{n+1})$<br>$=(\alpha^-)(T_n) \times 2+(\alpha^+)(T_{n+1})$ |
| | $(\beta^-)(T_n, T_{n+1}, T_{n+2})$<br>$=(\beta^-)(T_n) \times 2^2+(\beta^-)(T_{n+1}) \times 2+(\beta^-)(T_{n+2})$ | $(\beta^+)(T_n, T_{n+1})$<br>$=(\beta^+)(T_n) \times 2+(\beta^-)(T_{n+1})$ |
| | $(\beta^+)(T_n, T_{n+1}, T_{n+2})$<br>$=(\beta^+)(T_n) \times 2^2+(\beta^+)(T_{n+1}) \times 2+(\beta^+)(T_{n+2})$ | $(\beta^-)(T_n, T_{n+1})$<br>$=(\beta^-)(T_n) \times 2+(\beta^+)(T_{n+1})$ |
| | $(\gamma^-)(T_n, T_{n+1}, T_{n+2})$<br>$=(\gamma^-)(T_n) \times 2^2+(\gamma^-)(T_{n+1}) \times 2+(\gamma^-)(T_{n+2})$ | $(\gamma^+)(T_n, T_{n+1})$<br>$=(\gamma^+)(T_n) \times 2+(\gamma^-)(T_{n+1})$ |
| | $(\gamma^+)(T_n, T_{n+1}, T_{n+2})$<br>$=(\gamma^+)(T_n) \times 2^2+(\gamma^+)(T_{n+1}) \times 2+(\gamma^+)(T_{n+2})$ | $(\gamma^-)(T_n, T_{n+1})$<br>$=(\gamma^-)(T_n) \times 2+(\gamma^+)(T_{n+1})$ |

FIG. 10F

BRAINWAVE AUDIO AND VIDEO ENCODING AND PLAYING SYSTEM

FIELD OF THE INVENTION

The present invention is related to use of brainwaves, and in particular to a brainwave audio and video encoding and playing system.

BACKGROUND OF THE INVENTION

Currently, from research of brainwaves, it is knows that meditation, hearing ability, memory, logical ability, visual ability, reaction can be acquired from analysis of brainwaves. The brainwaves of human mainly include Delta wave, Theta waves, High/Low Alpha waves, High/Low Beta waves and High/Low Gamma waves of the left and right brains of the testers. These brainwaves have different physical, physiological, and psychological meanings, which expresses different conditions of the testers. Therefore, by measuring brainwaves and numerical operations thereto, characters and emotions of the testers can be got. These have been widely and deeply researched academically. The operations are executed in relative semiconductor chips.

Recently, concept of Metaverse abruptly become popular all over the world. One of the important features in Metaverse is how to imitate the human characters so as to make the virtual world more approaches the real world. It is known that Helmet brainwaves detectors can get the states of the brainwaves real time. By serial tests about emotions, reactions, and preference to find characters of human is a big trend in research of brainwaves. For example, Theta waves and Low Alpha waves are helpful to find the creations and inspiration of humans.

Therefore, since inventors of the present invention have worked in this field for many years and owns plentiful professional knowledge about these fields, they desire to propose a novel method which combines characters of brainwaves and digital coding systems so as to resolve problems encountered in the prior art.

SUMMARY OF THE INVENTION

Accordingly, the object of the present invention is to provide a brainwave audio and video encoding and playing system, wherein based on the research and understanding of the brainwaves of the inventors, they have find the relations of variations of the brainwaves corresponding to the melodies of the human voice senses and the relations of the human brainwaves to the colors so as to create above rules so that variations of the brainwaves can be expressed by playing of music and display of colors and the messages of brainwaves could be transferred. As a result, the people have the same feeling to the testers.

A brainwave audio and video encoding and playing system, comprises a helmet for detecting brainwaves of a tester, the helmet including a ring, a brainwave detector on the ring for detecting brainwaves and an attention and meditation calculator connected to the brainwave detector for calculating the attention level and meditation level of the tester, and a detector transceiver connected to the brainwave detector and the attention and meditation calculator for transmitting the brainwaves from the brainwave detector; a processing unit connected to the helmet for receiving the brainwave signals from the helmet and processing the signals; these brainwave signals including signals of brainwaves from the left brain and right brain of the tester, which contains Delta wave, Theta waves, High/Low Alpha waves, High/Low Beta waves and High/Low Gamma waves, and attention levels and meditation levels; the processor further including: a processor end transceiver connected to the detector transceiver of the helmet for receiving signals from the brainwave transceiver; a melody convertor connected to the processing end transceiver for converting the brainwave signals of the tester into respective music melodies by a specific algorithm, which is mainly based on the variations of Delta wave, Theta waves, High/Low Alpha waves, High/Low Beta waves and High/Low Gamma waves, and attention levels and meditation levels of the left and right brains of the tester; a color convertor connected to the processing end transceiver for converting brainwave signals of the tester into specific colors; a music player connected to the melody convertor for playing the music melodies from the melody convertor; a display unit connected to color convertor for displaying various colors from the cloud device.

BRIEF DESCRIPTION OF THE DRAWINGS

FIG. 4 is a table showing the strength differences calculated from the brainwave parameters according to the present invention.

FIG. 5 is an encoding table from the calculation of the encoding unit according to the present invention.

FIG. 6A shows a note conversion table in the first note set of the present invention.

FIG. 6B shows a note conversion table in the first note set of the present invention, which is a continuation of the table listed in FIG. 6A.

FIG. 7A shows a note conversion table in the second note set of the present invention.

FIG. 7B shows a note conversion table in the second note set of the present invention, which is a continuation of the table listed in FIG. 7A.

FIG. 7C shows a note conversion table in the second note set of the present invention, which is a continuation of the table listed in FIG. 7B.

FIG. 7D shows a note conversion table in the second note set of the present invention, which is a continuation of the table listed in FIG. 7C.

FIG. 7E shows a note conversion table in the second note set of the present invention, which is a continuation of the table listed in FIG. 7D.

FIG. 8A shows a note conversion table in the third note set of the present invention.

FIG. 8B shows a note conversion table in the third note set of the present invention, which is a continuation of the table listed in FIG. 8A.

FIG. 8C shows a note conversion table in the third note set of the present invention, which is a continuation of the table listed in FIG. 8B.

FIG. 8D shows a note conversion table in the third note set of the present invention, which is a continuation of the table listed in FIG. 8C.

FIG. 8E shows a note conversion table in the third note set of the present invention, which is a continuation of the table listed in FIG. 8D.

FIG. 9A shows a note conversion table in the fourth note set of the present invention.

FIG. 9B shows a note conversion table in the fourth note set of the present invention, which is a continuation of the table listed in FIG. 9A.

FIG. 9C shows a note conversion table in the fourth note set of the present invention, which is a continuation of the table listed in FIG. 9B.

FIG. 10A shows a beat conversion table of the present invention.

FIG. 10B shows a beat conversion table of the present invention, which is a continuation of the table listed in FIG. 10A.

FIG. 10C shows a beat conversion table of the present invention, which is a continuation of the table listed in FIG. 10B.

FIG. 10D shows a beat conversion table of the present invention, which is a continuation of the table listed in FIG. 10C.

FIG. 10E shows a beat conversion table of the present invention, which is a continuation of the table listed in FIG. 10D.

FIG. 10F shows a beat conversion table of the present invention, which is a continuation of the table listed in FIG. 10D.

DETAILED DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
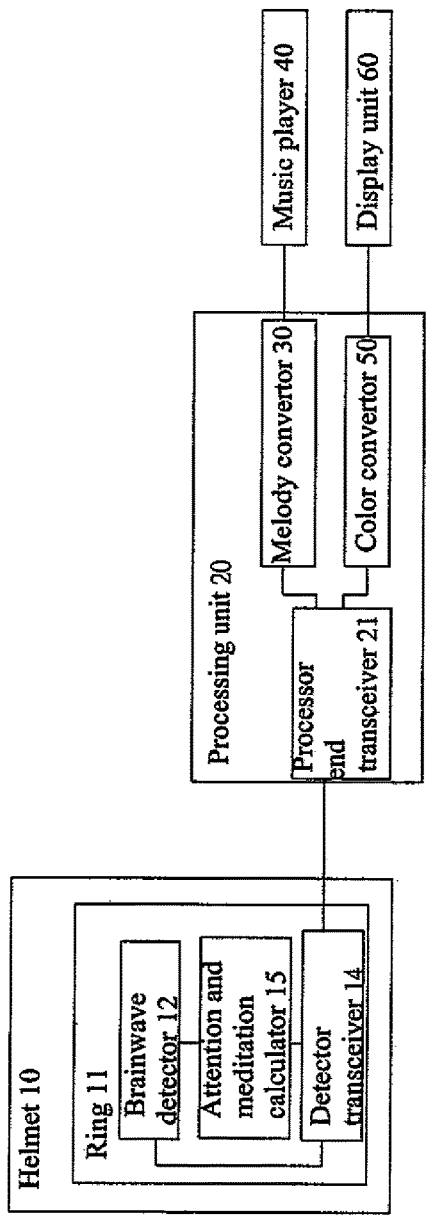
FIG. 1 is an assembled block diagram of the present invention.
Figure 2:
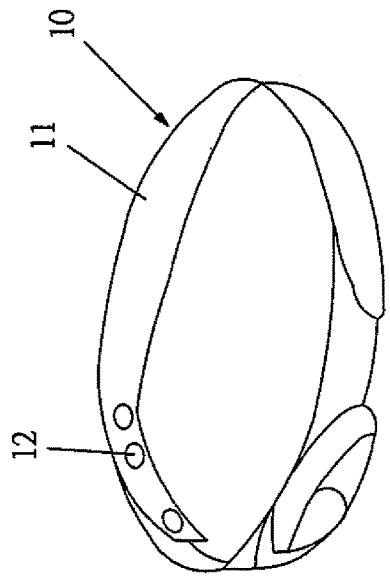
FIG. 2 is a schematic view showing the helmet of the present invention.
Figure 3:
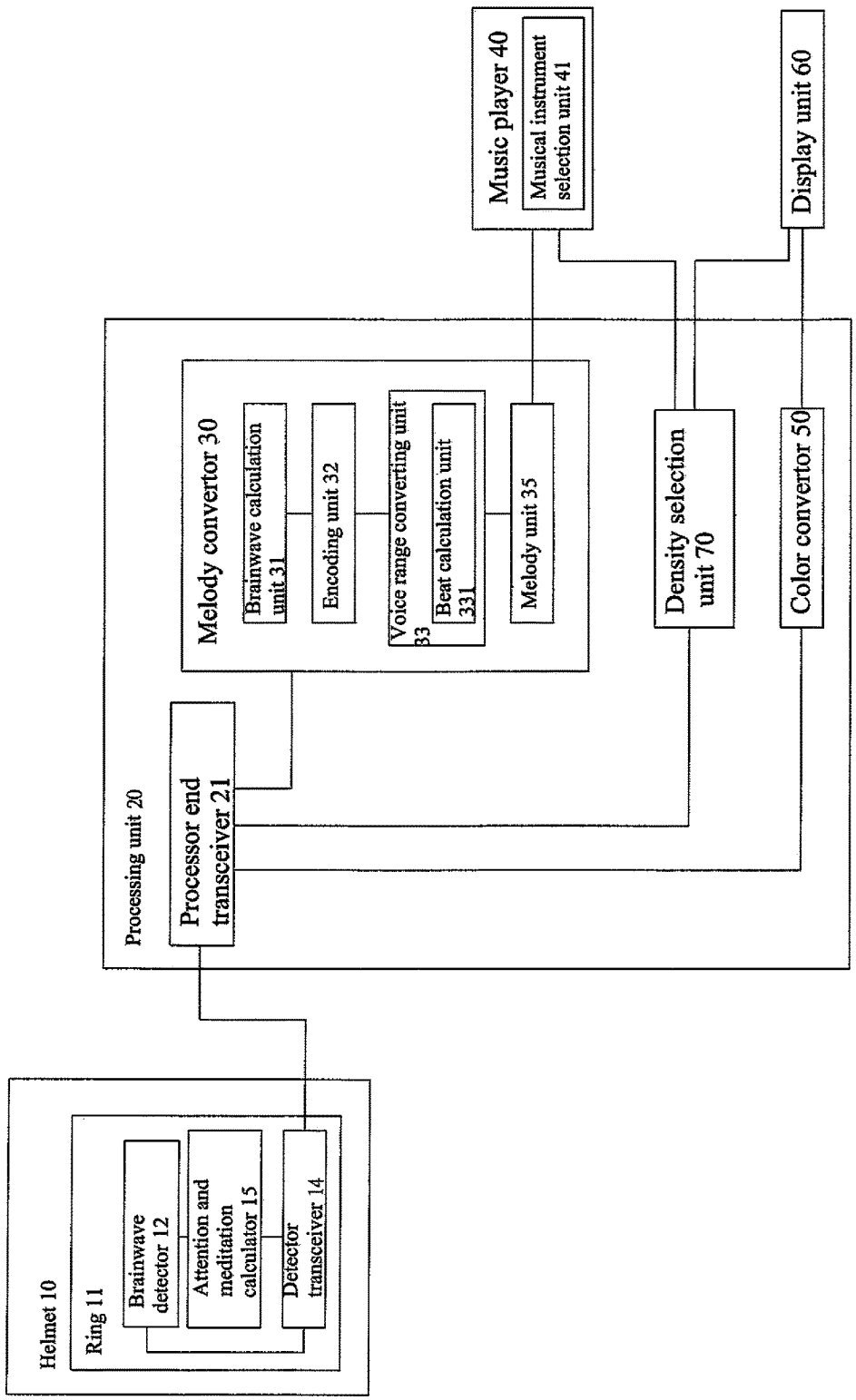
FIG. 3 is a schematic view showing the system block diagram of the present invention.

Referring to FIGS. 1 to 3, the structure of the present invention is illustrated. The present invention includes the following elements.

A helmet 10 serves to detect brainwaves of a tester. In use, the helmet 10 is worn on the head of the tester, as illustrated in FIGS. 1 and 2. The helmet 10 includes a ring 11, a brainwave detector 12 on the ring 11 for detecting brainwaves and an attention and meditation calculator 15 connected to the brainwave detector 12 for calculating the attention level and meditation level of the tester by known algorithm (which is known in the prior art and thus the details will not be further described herein), and a detector transceiver 14 connected to the brainwave detector 12 and the attention and meditation calculator 15 for transmitting the brainwaves from the brainwave detector 12.

A processing unit 20 connected to the helmet 10 receives the brainwave signals from the helmet 10 and processing the signals. These brainwave signals includes signals of brainwaves from the left brain and right brain of the tester, which contains Delta wave, Theta waves, High/Low Alpha waves, High/Low Beta waves and High/Low Gamma waves, and attention levels and meditation levels as shown in FIGS. 1 and 3. The processor 20 includes the following elements.

A processor end transceiver 21 connected to the detector transceiver 14 of the helmet 10 for receiving signals from the brainwave transceiver 14.

A melody convertor 30 connected to the processing end transceiver 21 for converting the brainwave signals of the tester into respective music melodies by a specific algorithm, which is mainly based on the variations of Delta wave, Theta waves, High/Low Alpha waves, High/Low Beta waves and High/Low Gamma waves, and attention levels and meditation levels of the left and right brains of the tester.

A color convertor 50 is connected to the processing end transceiver 21 for converting brainwave signals of the tester into specific colors.

A music player 40 is connected to the melody convertor 30 for playing the music melodies from the melody convertor 30.

A display unit 60 is connected to color convertor 50 for displaying various colors from the cloud device 10.

The processing unit 20 may be installed to various electronic devices, such as a computer, a mobile phone, a tablet computer, a PDA, etc.

The melody convertor 30 includes the following elements.

A brainwave calculation unit 31 serves to calculate brainwave strength difference Dt (where t is greater than 0) between two adjacent time points t−1 and t for various brainwave parameters Xs, wherein the brainwave parameter is selected from Att, Med, $\delta$, $\theta$, $\alpha-$, $\alpha+$, $\beta-$, $\beta+$, $\gamma-$, $\gamma+$, where the Att means the attention level, Med means the meditation level, and $\delta$ means Delta waves, $\theta$ means Theta waves, $\alpha-$ means Low Alpha waves, $\alpha+$ means High Alpha waves, $\beta-$ means Low Beta waves, $\beta+$ means High Beta waves, $\gamma-$ means Low Gamma waves, $\gamma+$ means High Gamma waves. The calculated values are illustrated in FIG. 4, wherein the calculation results of various brainwave parameters X for the DI to D are shown in the drawing.

An encoding unit 32 is connected to the brainwave calculation unit 31, wherein the variations of the strength differences of the brainwaves of different time periods with respective to the brainwave parameters X are encoded into respective binary values are illustrated, in that the time period Tn means Tth time period, and n is an integer greater than 0. The encoding unit 32 encodes these binary values into an encoding table, in that the brainwave parameters are listed as columns and the timer periods Tn are listed as row. Each binary values in the encoding table are expressed as X(Tn) or Tn(X), where X(Tn) expresses the binary value in the intersection lattice of the row of the brainwave parameter X and column of the time period Tn; and Tn(X) expresses the binary value in the intersection lattice of the column of the brainwave parameter X and row of the time period Tn. That is: the X(Tn) and Tn(X) are corresponding to the same binary value in the table.

The method for determining X(Tn) is that when Dn and Dn−1 are all larger than 0 or all smaller than 0 or all equal to 0, or Dn is greater than 0 and Dn−1 is equal to 0, or Dn is smaller than 0 and Dn−1 is equal to 0, then X(Tn) is equal to 0;

When one of Dn and Dn−1 is greater than 0 and another one is smaller than 0, or Dn is equal to 0 and Dn−1 is greater than 0, or Dn is equal to 0 and Dn−1 is smaller than 0, then X(Tn) is equal to 1.

The encoding table of the encoding unit 32 is illustrated in FIG. 5, wherein it is illustrated that the encoding results of each brainwave parameter in time period T1 to T7.

A voice range converting unit 33 is connected to the encoding unit 32. Based on values of the attention level and meditation level for each Tn in the encoding table, a respective voice range mode is selected. In each voice range mode, different converting rule is utilized to convert the binary value of the brainwave parameter X in the encoding table into respective note symbol and pitch in that time period Tn. Each note is converted from a binary value of at least one respective brainwave parameter.

The method for converting is that based on the value of Tn(Att, Med) Tn(Att, Med), the voice range mode of some specific time period Tn is determined, where Tn(Att, Med)=Tn(Att)×2+Tn(Med). Each voice range mode contains a plurality of note sets and each set of the note sets contains at least one respective note. The notes are generated by a specific way. Each note set has a treble range which covers a range of 8 pitches (but not means that each note set have 8 notes, each note corresponding to 1 pitch), and for two adjacent note set, the highest pitches of the two note sets have a difference of 8 pitches. Herein, the pitches in one note sets are defined from 0th pitch to 7th pitch.

The conversion of each voice range mode is as following:
When Tn(Att, Med)=0, it is the first voice range mode. It contains a first note set, a second note set, a third note set and a fourth note set, in that, pitches of the former note set are lower than the latter one.

The values of the notes in the first note set in the time period Tn is:

$$\delta(Tn) \times 22 + \delta(Tn+1) \times 2 + \delta(Tn+2), \text{ and}$$

$$\theta(Tn) \times 22 + \theta(Tn+1) \times 2 + \theta(Tn+2);$$

The values of the notes in the second note set in the time period Tn are:

$$(\alpha-)(Tn) \times 22 + (\alpha-)(Tn+1) \times 2 + (\alpha-)(Tn+2), \text{ and}$$

$$(\alpha+)(Tn) \times 22 + (\alpha+)(Tn+1) \times 2 + (\alpha+)(Tn+2);$$

The value of the notes in the third note set in the time period Tn are:

$$(\beta-)(Tn) \times 22 + (\beta-)(Tn+1) \times 2 + (\beta-)(Tn+2), \text{ and}$$

$$(\beta+)(Tn) \times 22 + (\beta+)(Tn+1) \times 2 + (\beta+)(Tn+2);$$

The values of the notes in the fourth note set in the time period Tn are:

$$(\gamma-)(Tn) \times 22 + (\gamma-)(Tn+1) \times 2 + (\gamma-)(Tn+2), \text{ and}$$

$$(\gamma+)(Tn) \times 22 + (\gamma+)(Tn+1) \times 2 + (\gamma+)(Tn+2).$$

The conversion results of the first voice range mode are shown in FIGS. 6A and 6B, in that the conversion result table of the time period is T1, T2, T3, T4 及 Tn.

When Tn(Att, Med)=1, it is a second voice range mode. It contains a first note set, a second note set, and a third note set, in that, pitches of the former note set are lower than the latter one. Herein, we define a brainwave parameter series K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki, for example, K4 expresses $\alpha+$, and K8 expresses $\gamma+$.

The values of the notes in the first note set in the time period Tn are:

$$(Att)(Tn) \times 22 + (Att)(Tn+1) \times 2 + (Att)(Tn+2), \text{ and}$$

$$(Med)(Tn) \times 22 + (Med)(Tn+1) \times 2 + (Med)(Tn+2);$$

The values of the notes in the second note set in the time period Tn are:

$$(Ki)(Tn) \times 22 + (Ki+1)(Tn) \times 2 + (Ki+2)(Tn), \text{ where } i=1\sim8.$$

The values of the notes in the third note set in the time period Tn are:

$$(Ki)(Tn) \times 22 + (Ki)(Tn+1) \times 2 + (Ki)(Tn+2), \text{ where } i=1\sim8.$$

The second and third note sets are converted into respective levels of pitches according to the value of i.

The conversion results of the second voice range are illustrated in FIGS. 7A to 7E, the conversion table for time periods T1, T2, T3 and Tn are illustrated.

When Tn(Att, Med)=2, it is a third voice range mode. It contains a first note set, a second note set, a third note set and a fourth note set according to the sequences of the pitches, in that, pitches of the former note set are lower than the latter ones. Herein, we define a brainwave parameter series K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki, for example, K4 expresses $\alpha+$, and K8 expresses $\gamma+$.

The values of the notes in the first note set in the time period Tn are:

$$(Att)(Tn) \times 22 + (Att)(Tn+1) \times 2 + (Att)(Tn+2), \text{ and}$$

$$(Med)(Tn) \times 22 + (Med)(Tn+1) \times 2 + (Med)(Tn+2);$$

The values of notes in the second note set in the time period Tn are:

$$(Ki)(Tn) \times 22 + (Ki+1)(Tn) \times 2 + (Ki+2)(Tn), \text{ wherein}=1\sim8.$$

The values of the notes in the third note set in the time period Tn are:

$$(Ki)(Tn) \times 22 + (Ki)(Tn+1) \times 2 + (Ki)(Tn+2), \text{ where } i=1\sim4.$$

The levels of pitches of the notes in the fourth note set in the time period Tn are:

$$(Ki)(Tn) \times 22 + (Ki)(Tn+1) \times 2 + (Ki)(Tn+2), \text{ where } i=5\sim8.$$

The second, third and fourth note sets are converted into respective notes according to the value of i.

The conversion results of the second voice range are illustrated in FIGS. 8A to 8E, the conversion table for time periods T1, T2, T3 and Tn are illustrated.

When Tn(Att, Med)=3, it is a fourth voice range mode. It contains a first note set, a second note set, a third note set and a fourth note set according to the sequences of the pitches, in that, pitches of the former note set are lower than the latter ones. Herein, we define a brainwave parameter series K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki, for example, K4 expresses $\alpha+$, and K8 expresses $\gamma+$.

The values of the notes in the first note set in the time period Tn are:

$$(Ki)(Tn) \times 22 + (Ki+1)(Tn) \times 2 + (Ki+2)(Tn), \text{ where } i=1\sim4.$$

The values of the notes in the second note set in the time period Tn are:

$$(Ki)(Tn) \times 22 + (Ki+1)(Tn) \times 2 + (Ki+2)(Tn), \text{ where } i=5\sim8.$$

The values of the notes in the third note set in the time period Tn are:

$$(Ki)(Tn) \times 22 + (Ki)(Tn+1) \times 2 + (Ki)(Tn+2), \text{ where } i=1\sim4.$$

The values of the notes in the fourth note set in the time period Tn are:

$$(Ki)(Tn) \times 22 + (Ki)(Tn+1) \times 2 + (Ki)(Tn+2), \text{ where } i=5\sim8.$$

The note sets are converted into respective pitches according to the value of i.

The conversion results of the fourth voice range are illustrated in FIGS. 9A to 9E, the conversion table for time periods T1, T2, T3 and Tn are illustrated.

The voice range conversion unit 33 further includes a beat calculation unit 331 for calculation of beats according to the conversion rules said above of the notes.

The 0 define as a complete one beat, 1 defines as a ½ beat, 2 defined as a ¼ beat, 3 expresses ⅛ beats.

The way for calculation of beats in the beat calculation unit 331 is that:

As the note has the conversion rule of (Att)(Tn)×22+(Att)(Tn+1)×2+(Att)(Tn+2), then the beat is (Med)(Tn)×2+(Med)(Tn+1).

As the note has the conversion rule of (Med)(Tn)×22+(Med)(Tn+1)×2+(Med)(Tn+2), then the beat is (Att)(Tn)×2+(Att)(Tn+1).

As the note has the conversion rule of (Ki)(Tn)×22+(Ki+1)(Tn)×2+(Ki+2)(Tn), then the beat is (Ki+3)(Tn)×2+(Ki+4)(Tn), where i=1~8.

As the note has the conversion rule of δ(Tn)×22+δ(Tn+1)×2+δ(Tn+2), then the beat is θ(Tn)×2+θ(Tn+1).

As the note has the conversion rule of θ(Tn)×22+θ(Tn+1)×2+θ(Tn+2), then the beat is δ(Tn)×2+δ(Tn+1).

As the note has the conversion rule of (α−)(Tn)×22+(α−)(Tn+1)×2+(α−)(Tn+2), then the beat is (α+)(Tn)×2+(α+)(Tn+1).

As the note has the conversion rule of (α+)(Tn)×22+(α+)(Tn+1) 2+(α+)(Tn+2), then the beat is (α−)(Tn)×2+(α−)(Tn+1).

As the note has the conversion rule of (β−)(Tn)×22+(β−)(Tn+1)×2+(β−)(Tn+2), then the beat is (β+)(Tn)×2+(β+)(Tn+1).

As the note has the conversion rule of ((3+)(Tn)×22+(β+)(Tn+1)×2+(β+)(Tn+2), then the beat is (β−)(Tn)×2+(β−)(Tn+1).

As the note has the conversion rule of (γ−)(Tn)×22+(γ−)(Tn+1)×2+(γ−)(Tn+2), then the beat is (γ+)(Tn)×2+(γ+)(Tn+1).

As the note has the conversion rule of (γ+)(Tn)×22+(γ+)(Tn+1)×2+(γ+)(Tn+2), then the beat is (γ−)(Tn)×2+(γ−)(Tn+1).

The conversion result of the beat calculation unit is listed in FIG. 10A to 10F, where the conversion table of time periods T1 及 T2 and Tn are illustrated.

A melody unit 35 is connected to the voice range conversion unit 33 for arranging the notes of different time period Tn converted from the voice range conversion unit 33 based on specific sequence so as to build music melodies in various Tn. Then the melodies are outputted to the music player 40.

The way of arrangement of the notes in a some Tn is based on the values of Tn+1(Att, Med), where Tn+1(Att, Med)=Tn+1(Att)×2+Tn+1(Med).

When Tn+1(Att, Med)=0, then notes in the note set with respective to the Tn is arranged according to the level of the pitch of the note.

If the pitch of note in the note set is converted from one single brainwave parameter Y, wherein the brainwave parameter is selected from δ, θ, α−, α+, β−, β+, γ−, γ+, for example, the pitch of the note in the first note set of the first voice range mode δ(Tn)×22+δ(Tn+1)×2+δ(Tn+2), and θ(Tn)×22+θ(Tn−1)×2+θ(Tn−2), then these notes are arranged based on the respective brainwave parameters δ, θ, α−, α+, β−, β+, γ−, γ+.

If the notes in the note set are not converted from above said one single brainwave parameter Y, then these notes are arranged form the first note to the last note based on the sequence of generation of these notes. For example, the values of notes in the second note set of the second voice range are (Ki)(Tn)×22+(Ki+1)(Tn)×2+(Ki+2)(Tn), they are arranged according to the sequence of i=1~8.

When Tn+1(Att, Med)=1, then the first note in time period Tn is arranged in the first time point, and second note in time period Tn is arranged in the second time point, the processes are executed to the Mth note, where M is greater than 0. When the numbers of notes of different note sets in time period Tn are different, for the number of the notes in the note set is smaller than the other note set, as all the notes in that note set is used up, then the sequence of using notes is circulated to the former notes. The music player 40 can play the notes so as to have the effect of mixing of the different notes.

When Tn+1(Att, Med)=2, all the notes with respective to the time period Tn are arranged from higher pitch to lower pitch based on the levels of the pitches of the notes in all the note sets. Then these notes are arranged from the first note to the last note in all the note sets based on the levels of the pitches, and then the sequence is further arranged by a reverse order as they are generated, that is, from the last note to the first note. They are arranged repeatedly by above mentioned way.

When Tn+1(Att, Med)=3, all the notes with respective to the time period Tn are arranged from higher pitch to lower pitch based on the levels of the pitches of the notes in all the note sets.

For all the notes in all the note sets, if each note is converted from a single one brainwave parameter Z, and Z is selected from γ+, γ−, β+, β−, α+, α−, θ. δ for example, notes in the first note set in the first voice range mode are δ(Tn)×22+δ(Tn+1)×2+δ(Tn+2), θ(Tn)×22+θ(Tn+1)×2+θ(Tn+2), then these notes are arranged based on the respective brainwave parameters γ+, γ−, β+, β−, α+, α−, θ. δ.

For all the notes in all the note sets, if all the notes are not converted from a single one brainwave parameter Z, then these notes are reversed based on the sequence generating these notes, that is arranged from the last note to the first note, for example, for all notes in the first note sets in the second voice range modes, (Ki)(Tn)×22+(Ki+1)(Tn)×2+(Ki+2)(Tn), they are arranged based on a reverse order, that is to say based on the sequence i=8~1.

The color conversion unit 50 serves to map different sections of the brainwaves to different colors, wherein Delta wave is mapped to white color, Theta is mapped to red color, Low Alpha is mapped to orange color, High Alpha is mapped to yellow color, Low Beta is mapped to green color, High Beta is mapped to blue color, Low Gamma is mapped to indigo color, and High Gamma is mapped to purple color. When the music player 40 plays music, it transfers respective colors to the display unit 60 based on the brainwave sections corresponding to the notes.

The processing unit 20 further includes a voice volume and color density selection unit 70 which is connected to the music player 40 and the display unit 60 for classifying the values of the brainwave parameters in different time periods into different classes based on amplitude of the brainwaves. Different classes are corresponding to different volume and color density for controlling the volume of the music player 40 and the color density of the display unit 60.

The music player 40 further includes a musical instrument selection unit 41 for selection of the musical instrument from the tester and the timbre of the music instrument is sued to play the melody determined above. Therefore, when there are a plurality of testers, various music instruments are selected and combined to play the melodies from these testers.

The music player 40 could play the melody from the melody converter 30 by MIDI format.

In the present invention, based on the research and understanding of the brainwaves of the inventors, they have find the relations of variations of the brainwaves corresponding to the melodies of the human voice senses and the relations of the human brainwaves to the colors so as to create above rules so that variations of the brainwaves can be expressed by playing of music and display of colors and the messages of brainwaves could be transferred. As a result, the people have the same feeling to the testers.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A brainwave audio and video encoding and playing system, comprising:
    a helmet for detecting brainwaves of a tester, the helmet including a ring, a brainwave detector on the ring for detecting brainwaves and an attention and meditation calculator connected to the brainwave detector for calculating the attention level and meditation level of the tester, and a detector transceiver connected to the brainwave detector and the attention and meditation calculator for transmitting the brainwaves from the brainwave detector;
    a processing unit connected to the helmet for receiving the brainwave signals from the helmet and processing the signals; these brainwave signals including signals of brainwaves from the left brain and right brain of the tester, which contains Delta wave, Theta waves, High/Low Alpha waves, High/Low Beta waves and High/Low Gamma waves, and attention levels and meditation levels;
    the processor further including:
    a processor end transceiver connected to the detector transceiver of the helmet for receiving signals from the brainwave transceiver;
    a melody convertor connected to the processing end transceiver for converting the brainwave signals of the tester into respective music melodies by a specific algorithm, which is mainly based on the variations of Delta wave, Theta waves, High/Low Alpha waves, High/Low Beta waves and High/Low Gamma waves, and attention levels and meditation levels of the left and right brains of the tester;
    a color convertor connected to the processing end transceiver for converting brainwave signals of the tester into specific colors;
    a music player connected to the melody convertor for playing the music melodies from the melody convertor;
    a display unit connected to color convertor for displaying various colors from the cloud device.

2. The brainwave audio and video encoding and playing system as claimed in claim 1, wherein the melody convertor including:
    a brainwave calculation unit for calculating brainwave strength difference Dt (where t is greater than 0) between two adjacent time points t−1 and t for various brainwave parameters Xs, wherein the brainwave parameter is selected from Att, Med, δ, θ, α−, α+, β−, β+, γ−, γ+, where the Att means the attention level, Med means the meditation level, and δ means Delta waves, θ means Theta waves, α− means Low Alpha waves, α+ means High Alpha waves, β− means Low Beta waves, β+ means High Beta waves, γ− means Low Gamma waves, γ+ means High Gamma waves;
    an encoding unit connected to the brainwave calculation unit, wherein variations of strength differences of the brainwaves of different time periods with respective to the brainwave parameters X are encoded into respective binary values are illustrated, in that the time period Tn means Tth time period, and n is an integer greater than 0; the encoding unit encodes these binary values into an encoding table, in that the brainwave parameters are listed as columns and the timer periods Tn are listed as row; each binary values in the encoding table are expressed as X(Tn) or Tn(X), where X(Tn) expresses the binary value in the intersection lattice of the row of the brainwave parameter X and column of the time period Tn; and Tn(X) expresses the binary value in the intersection lattice of the column of the brainwave parameter X and row of the time period Tn; that is: the X(Tn) and Tn(X) are corresponding to the same binary value in the table;
    a voice range converting unit connected to the encoding unit; based on values of the attention level and meditation level for each Tn in the encoding table, a respective voice range mode being selected; in each voice range mode, different converting rule being-utilized to convert the binary value of the brainwave parameter X in the encoding table into respective note symbol and pitch in that time period Tn; each note is converted from a binary value of at least one respective brainwave parameter; and
    a melody unit connected to the voice range conversion unit for arranging the notes of different time period Tn converted from the voice range conversion unit based on a specific sequence so as to build music melodies in various Tn; and then the melodies are outputted to the music player.

3. The brainwave audio and video encoding and playing system as claimed in claim 2, wherein in the encoding unit, the method for determining X(Tn) is that when Dn and Dn−1 are all larger than 0 or all smaller than 0 or all equal to 0, or Dn is greater than 0 and Dn−1 is equal to 0, or Dn is smaller than 0 and Dn−1 is equal to 0, then X(Tn) is equal to 0; and when one of Dn and Dn−1 is greater than 0 and another one is smaller than 0, or Dn is equal to 0 and Dn−1 is greater than 0, or Dn is equal to 0 and Dn−1 is smaller than 0, then X(Tn) is equal to 1.

4. The brainwave audio and video encoding and playing system as claimed in claim 2, wherein in the voice range converting unit, the method for converting is that based on the value of Tn(Att, Med), the voice range mode of some specific time period Tn is determined, where Tn(Att, Med) =Tn(Att)×2+Tn(Med); each voice range mode contains a plurality of note sets and each set of the note sets contains at least one respective note; the notes are generated by a specific way; each note set has a treble range which covers a range of 8 pitches, and for two adjacent note set, the highest pitches of the two note sets have a difference of 8 pitch; the pitches in one note sets are defined from 0th pitch to 7th pitch; a brainwave parameter series is defined as K="δ, θ, α−, α+, β−, β+, γ−, γ+, δ, θ, α−, α+", in that the ith element in the K series is expressed by Ki.

5. The brainwave audio and video encoding and playing system as claimed in claim 4, wherein when Tn(Att, Med) =0, a first voice range mode is defined and contains a first note set, a second note set, a third note set and a fourth note set, in that, pitches of the former note set are lower than the latter one; wherein values of the notes in the first note set in the time period Tn is:

$$\delta(Tn) \times 22 + \delta(Tn+1) \times 2 + \delta(Tn+2), \text{ and}$$

$$\theta(Tn) \times 22 + \theta(Tn+1) \times 2 + \theta(Tn+2);$$

values of the notes in the second note set in the time period Tn are:

$$(\alpha-)(Tn) \times 22 + (\alpha-)(Tn+1) \times 2 + (\alpha-)(Tn+2), \text{ and}$$

$$(\alpha+)(Tn) \times 22 + (\alpha+)(Tn+1) \times 2 + (\alpha+)(Tn+2);$$

value of the notes in the third note set in the time period Tn are:

$$(\beta-)(Tn) \times 22 + (\beta-)(Tn+1) \times 2 + (\beta-)(Tn+2), \text{ and}$$

$$(\beta+)(Tn) \times 22 + (\beta+)(Tn+1) \times 2 + (\beta+)(Tn+2); \text{ and}$$

values of the notes in the fourth note set in the time period Tn are:

$$(\gamma-)(Tn) \times 22 + (\gamma-)(Tn+1) \times 2 + (\gamma-)(Tn+2), \text{ and}$$

$$(\gamma+)(Tn) \times 22 + (\gamma+)(Tn+1) \times 2 + (\gamma+)(Tn+2).$$

6. The brainwave audio and video encoding and playing system as claimed in claim 4, wherein when Tn(Att, Med)=1, a second voice range mode is defined and contains a first note set, a second note set, and a third note set, in that, pitches of the former note set are lower than the latter one, a brainwave parameter series is defined as K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki;

values of the notes in the first note set in the time period Tn are:

$$(Att)(Tn) \times 22 + (Att)(Tn+1) \times 2 + (Att)(Tn+2), \text{ and}$$

$$(Med)(Tn) \times 22 + (Med)(Tn+1) \times 2 + (Med)(Tn+2);$$

values of the notes in the second note set in the time period Tn are:

$$(Ki)(Tn) \times 22 + (Ki+1)(Tn) \times 2 + (Ki+2)(Tn), \text{ where } i=1 \text{ to } 8;$$

values of the notes in the third note set in the time period Tn are:

$$(Ki)(Tn) \times 22 + (Ki)(Tn+1) \times 2 + (Ki)(Tn+2), \text{ where } i=1 \text{ to } 8; \text{ and}$$

the second and third note sets are converted into respective levels of pitches according to the value of i.

7. The brainwave audio and video encoding and playing system as claimed in claim 4, wherein when Tn(Att, Med)=2, a third voice range mode is defined and contains a first note set, a second note set, a third note set and a fourth note set according to the sequences of the pitches, in that, pitches of the former note set are lower than the latter ones, a brainwave parameter series is defined as K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki, wherein values of the notes in the first note set in the time period Tn are:

$$(Att)(Tn) \times 22 + (Att)(Tn+1) \times 2 + (Att)(Tn+2), \text{ and}$$

$$(Med)(Tn) \times 22 + (Med)(Tn+1) \times 2 + (Med)(Tn+2);$$

values of notes in the second note set in the time period Tn are:

$$(Ki)(Tn) \times 22 + (Ki+1)(Tn) \times 2 + (Ki+2)(Tn), \text{ wherein}=1 \text{ to } 8;$$

The values of the notes in the third note set in the time period Tn are:

$$(Ki)(Tn) \times 22 + (Ki)(Tn+1) \times 2 + (Ki)(Tn+2), \text{ where } i=1 \text{ to } 4;$$

levels of pitches of the notes in the fourth note set in the time period Tn are:

$$(Ki)(Tn) \times 22 + (Ki)(Tn+1) \times 2 + (Ki)(Tn+2), \text{ where } i=5\sim8; \text{ and}$$

the second, third and fourth note sets are converted into respective notes according to the value of i.

8. The brainwave audio and video encoding and playing system as claimed in claim 4, wherein when Tn(Att, Med)=3, a fourth voice range mode is defined and contains a first note set, a second note set, a third note set and a fourth note set according to the sequences of the pitches, in that, pitches of the former note set are lower than the latter ones, a brainwave parameter series is defined as K="$\delta$, $\theta$, $\alpha-$, $\alpha+$, $\beta-$, $\beta+$, $\gamma-$, $\gamma+$, $\delta$, $\theta$, $\alpha-$, $\alpha+$", in that the ith element in the K series is expressed by Ki; wherein values of the notes in the first note set in the time period Tn are:

$$(Ki)(Tn) \times 22 + (Ki+1)(Tn) \times 2 + (Ki+2)(Tn), i=1\sim4;$$

values of the notes in the second note set in the time period Tn are:

$$(Ki)(Tn) \times 22 + (Ki+1)(Tn) \times 2 + (Ki+2)(Tn), \text{ where } i=5 \text{ to } 8;$$

values of the notes in the third note set in the time period Tn are:

$$(Ki)(Tn) \times 22 + (Ki)(Tn+1) \times 2 + (Ki)(Tn+2), \text{ where } i=1 \text{ to } 4; \text{ and}$$

values of the notes in the fourth note set in the time period Tn are:

$$(Ki)(Tn) \times 22 + (Ki)(Tn+1) \times 2 + (Ki)(Tn+2), \text{ where } i=5 \text{ to } 8; \text{ and}$$

the note sets are converted into respective pitches according to the value of i.

9. The brainwave audio and video encoding and playing system as claimed in claim 5, wherein the voice range conversion unit further includes a beat calculation unit for calculation of beats according to the conversion rules said above of the notes.

10. The brainwave audio and video encoding and playing system as claimed in claim 9, wherein 0 define as a complete one beat, 1 defines as a ½ beat, 2 defined as a ¼ beat, 3 expresses ⅛ beats; and a way for calculation of beats in the beat calculation unit is that:

as the note has a conversion rule of $(Att)(Tn) \times 22 + (Att)(Tn+1) \times 2 + (Att)(Tn+2)$, then the beat is $(Med)(Tn) \times 2 + (Med)(Tn+1)$;

as the note has a conversion rule of $(Med)(Tn) \times 22 + (Med)(Tn+1) \times 2 + (Med)(Tn+2)$, then the beat is $(Att)(Tn) \times 2 + (Att)(Tn+1)$;

as the note has a conversion rule of $(Ki)(Tn) \times 22 + (Ki+1)(Tn) \times 2 + (Ki+2)(Tn)$, then the beat is $(Ki+3)(Tn) \times 2 + (Ki+4)(Tn)$, where $i=1\sim8$;

as the note has a conversion rule of $\delta(Tn) \times 22 + \delta(Tn+1) \times 2 + \delta(Tn+2)$, then the beat is $\theta(Tn) \times 2 + \theta(Tn+1)$;

as the note has a conversion rule of θ(Tn)×22+θ(Tn+1)× 2+θ(Tn+2), then the beat is δ(Tn)×2+δ(Tn+1);

as the note has a conversion rule of (α−)(Tn)×22+(α−)(Tn+1)×2+(α−)(Tn+2), then the beat is (α+)(Tn)×2+(α+)(Tn+1);

as the note has a conversion rule of (α+)(Tn)×22+(α+)(Tn+1)×2+(α+)(Tn+2), then the beat is (α−)(Tn)×2+(α−)(Tn+1);

as the note has a conversion rule of (β−)(Tn)×22+(β−)(Tn+1)×2+(β−)(Tn+2), then the beat is (β+)(Tn)×2+(β+)(Tn+1);

As the note has a conversion rule of (β+)(Tn)×22+(β+)(Tn+1)×2+(β+)(Tn+2), then the beat is (β−)(Tn)×2+(β−)(Tn+1);

as the note has a conversion rule of (γ−)(Tn)×22+(γ−)(Tn+1)×2+(γ−)(Tn+2), then the beat is (γ+)(Tn)×2+(γ+)(Tn+1); and as the note has a conversion rule of (γ+)(Tn)×22+(γ+)(Tn+1)×2+(γ+)(Tn+2), then the beat is (γ−)(Tn)×2+(γ−)(Tn+1).

11. The brainwave audio and video encoding and playing system as claimed in claim 5, wherein in the melody unit, a way of arrangement of the notes in a Tn is based on the values of Tn+1(Att, Med), where Tn+1(Att, Med)=Tn+1(Att)×2+Tn+1(Med); and when Tn+1(Att, Med)=0, then notes in the note set with respective to the Tn is arranged according to the level of the pitch of the note;

if the pitch of note in the note set is converted from one single brainwave parameter Y, wherein the brainwave parameter is selected from δ, θ, α−, α+, β−, β+, γ−, γ+, then these notes are arranged based on the respective brainwave parameters δ, θ, α−, α+, β−, β+, γ−, γ+;

if the notes in the note set are not converted from above said one single brainwave parameter Y, then these notes are arranged form the first note to the last note based on the sequence of generation of these notes;

when Tn+1(Att, Med)=1, then the first note in time period Tn is arranged in the first time point, and second note in time period Tn is arranged in the second time point, the processes are executed to the Mth note, where M is greater than 0; when the numbers of notes of different note sets in time period Tn are different, for the number of the notes in the note set is smaller than the other note set, as all the notes in that note set is used up, then the sequence of using notes is circulated to the former notes; and the music player is able to play the notes so as to have the effect of mixing of the different notes;

when Tn+1(Att, Med)=2, all the notes with respective to the time period Tn are arranged from higher pitch to lower pitch based on the levels of the pitches of the notes in all the note sets; then these notes are arranged from the first note to the last note in all the note sets based on the levels of the pitches, and then the sequence is further arranged by a reverse order as they are generated, that is, from the last note to the first note; and they are arranged repeatedly by above mentioned way;

when Tn+1(Att, Med)=3, all the notes with respective to the time period Tn are arranged from higher pitch to lower pitch based on the levels of the pitches of the notes in all the note sets; and for all the notes in all the note sets, if each note is converted from a single one brainwave parameter Z, and Z is selected from γ−, γ−, β+, β−, α+, α−, θ, δ, then these notes are arranged based on the respective brainwave parameters γ+, γ−, β+, β−, α+, α−, θ, δ; and for all the notes in all the note sets, if all the notes are not converted from a single one brainwave parameter Z, then these notes are reversed based on the sequence generating these notes, that is arranged from the last note to the first note, they are arranged based on a reverse order, that is to say based on the sequence i=8 to 1.

12. The brainwave audio and video encoding and playing system as claimed in claim 2, wherein the color conversion unit serves to map different sections of the brainwaves to different colors, wherein Delta wave is mapped to white color, Theta is mapped to red color, Low Alpha is mapped to orange color, High Alpha is mapped to yellow color, Low Beta is mapped to green color, High Beta is mapped to blue color, Low Gamma is mapped to indigo color, and High Gamma is mapped to purple color; and when the music player plays music, it transfers respective colors to the display unit based on the brainwave sections corresponding to the notes.

13. The brainwave audio and video encoding and playing system as claimed in claim 1, wherein the processing unit further includes a voice volume and color density selection unit which is connected to the music player and the display unit for classifying the values of the brainwave parameters in different time periods into different classes based on amplitude of the brainwaves; different classes are corresponding to different volume and color density for controlling the volume of the music player and the color density of the display unit.

14. The brainwave audio and video encoding and playing system as claimed in claim 1, wherein the music player further includes a musical instrument selection unit for selection of the musical instrument from the tester and the timbre of the music instrument is used to play the melody; and therefore, when there are a plurality of testers, various music instruments are selected and combined to play the melodies from these testers.

* * * * *